US010760182B2

(12) United States Patent
Tran et al.

(10) Patent No.: US 10,760,182 B2
(45) Date of Patent: Sep. 1, 2020

(54) METHOD AND DEVICE FOR MARKING FIBROUS MATERIALS

(71) Applicant: APDN (B.V.I.) Inc., Tortola (VG)

(72) Inventors: Alex Phidung Tran, East Setauket, NY (US); Abdelkrim Berrada, Lake Ronkonkoma, NY (US); MingHwa Benjamin Liang, East Setauket, NY (US); Lawrence Jung, Forest Hills, NY (US)

(73) Assignee: APDN (B.V.I.) INC., Tortola (VG)

( * ) Notice: Subject to any disclaimer, the term of this patent is extended or adjusted under 35 U.S.C. 154(b) by 538 days.

(21) Appl. No.: 14/572,552

(22) Filed: Dec. 16, 2014

(65) Prior Publication Data

US 2016/0168781 A1    Jun. 16, 2016

(51) Int. Cl.
*C12Q 1/68* (2018.01)
*D01B 1/04* (2006.01)
(Continued)

(52) U.S. Cl.
CPC ............... *D01B 1/04* (2013.01); *C12Q 1/68* (2013.01); *D01B 9/00* (2013.01); *D01G 99/00* (2013.01);
(Continued)

(58) Field of Classification Search
None
See application file for complete search history.

(56) References Cited

U.S. PATENT DOCUMENTS 2,834,058 A * 5/1958 Bryant ................. D01G 99/005
19/39
4,183,989 A 1/1980 Tooth
(Continued)

FOREIGN PATENT DOCUMENTS

CN    102453982 B    10/2013
EP    0 477 220 B1    4/1992
(Continued)

OTHER PUBLICATIONS

Karim Berrada et al., "ICAC Recorder; 2010 IIS 1840-P2; ISSN 1022-6303", Sep. 29, 2013, XP055463650, retrieved from the internet; URL:https://www.icac.org/getattachment/mtgs/Plenary/72nd-Plenary/Presentations/Pap-KBerrarda-DNA.pdf.
(Continued)

*Primary Examiner* — Robert T. Crow
(74) *Attorney, Agent, or Firm* — Clay D. Shorrock

(57) ABSTRACT

A method of marking fibers, wherein the method includes providing a plurality of fibers; depositing a marker onto at least a portion of the fibers, the depositing being performed with a delivery mechanism comprising one or more outlets; and thereby marking the fibers. Also provided is a device for marking fibers, including a transport system adapted to transport fibers in a direction of a marker delivery apparatus positioned along the transport system; the delivery apparatus includes one or more outlets, adapted to deposit a solution of the marker through the outlets onto at least a portion of the fibers; and thereby marking the fibers. Authentication of a fibrous material using the marking method of the invention followed obtaining a sample of the marked fibers and assaying the sample for the presence of the nucleic acid marker; and thereby determining whether the fibrous material is authentic or counterfeit.

9 Claims, 11 Drawing Sheets

(51) Int. Cl.
*D06M 15/01* (2006.01)
*D06M 16/00* (2006.01)
*D01G 99/00* (2010.01)
*D01B 9/00* (2006.01)
*D06H 1/00* (2006.01)
*D06M 101/12* (2006.01)
*D06M 101/06* (2006.01)

(52) U.S. Cl.
CPC .............. *D06H 1/00* (2013.01); *D06M 15/01* (2013.01); *D06M 16/00* (2013.01); *D06M 2101/06* (2013.01); *D06M 2101/12* (2013.01)

(56) References Cited

U.S. PATENT DOCUMENTS

| | | | |
|---|---|---|---|
| 4,278,557 A | 7/1981 | Elwell, Jr. | |
| 4,548,955 A | 10/1985 | Okahata | |
| 4,739,044 A | 4/1988 | Stabinsky | |
| 4,757,141 A | 7/1988 | Fung et al. | |
| 5,047,519 A | 9/1991 | Hobbs, Jr. et al. | |
| 5,089,691 A | 2/1992 | Morisaki et al. | |
| 5,132,242 A | 7/1992 | Cheung | |
| 5,139,812 A | 8/1992 | Lebacq | |
| 5,151,507 A | 9/1992 | Hobbs, Jr. et al. | |
| 5,429,952 A | 7/1995 | Garner et al. | |
| 5,451,505 A | 9/1995 | Dollinger | |
| 5,498,283 A | 3/1996 | Botros et al. | |
| 5,595,871 A | 1/1997 | DelVecchio et al. | |
| 5,599,578 A | 2/1997 | Butland | |
| 5,602,381 A | 2/1997 | Hoshino et al. | |
| 5,639,603 A | 6/1997 | Dower et al. | |
| 5,643,728 A | 7/1997 | Slater et al. | |
| 5,763,176 A | 6/1998 | Slater et al. | |
| 5,776,713 A | 7/1998 | Garner et al. | |
| 5,866,336 A | 2/1999 | Nazarenko et al. | |
| 5,942,444 A | 8/1999 | Rittenburg et al. | |
| 5,989,823 A | 11/1999 | Jayasena et al. | |
| 6,013,789 A | 1/2000 | Rampal | |
| 6,030,657 A | 2/2000 | Butland et al. | |
| 6,057,370 A | 5/2000 | Weiland et al. | |
| 6,127,120 A | 10/2000 | Graham et al. | |
| 6,140,075 A | 10/2000 | Russell et al. | |
| 6,169,174 B1 | 1/2001 | Hasegawa et al. | |
| 6,237,195 B1* | 5/2001 | Shoemaker | D01B 1/06 19/66 CC |
| 6,251,639 B1* | 6/2001 | Kurn | C12Q 1/6844 435/6.1 |
| 6,261,809 B1 | 7/2001 | Bertling et al. | |
| 6,312,911 B1 | 11/2001 | Bancroft et al. | |
| 6,342,359 B1 | 1/2002 | Lee et al. | |
| 6,397,437 B1* | 6/2002 | Shofner | D01G 31/006 19/66 CC |
| 6,399,397 B1 | 6/2002 | Zarling et al. | |
| 6,576,422 B1 | 6/2003 | Weinstein et al. | |
| 6,686,149 B1 | 2/2004 | Sanchis et al. | |
| 6,703,228 B1 | 3/2004 | Landers | |
| 6,743,640 B2 | 6/2004 | Whitten et al. | |
| 6,995,256 B1 | 2/2006 | Li et al. | |
| 7,031,927 B1 | 4/2006 | Beck et al. | |
| 7,060,874 B2 | 6/2006 | Wilkins | |
| 7,115,301 B2 | 10/2006 | Sheu et al. | |
| 7,160,996 B1 | 1/2007 | Cook | |
| 7,223,906 B2 | 5/2007 | Davis | |
| 7,250,195 B1 | 7/2007 | Storey et al. | |
| 7,732,492 B2 | 6/2010 | Makino et al. | |
| 8,278,807 B2 | 10/2012 | Agneray et al. | |
| 9,297,032 B2 | 3/2016 | Jung | |
| 9,963,740 B2* | 5/2018 | Berrada | C12Q 1/6816 |
| 2001/0039018 A1 | 11/2001 | Matson et al. | |
| 2002/0048822 A1 | 4/2002 | Rittenburg et al. | |
| 2002/0064639 A1 | 5/2002 | Rearick | |
| 2002/0081597 A1* | 6/2002 | Lowe | B01J 19/0046 435/6.12 |
| 2002/0119485 A1 | 8/2002 | Morgan | |
| 2002/0128234 A1 | 9/2002 | Hubbell et al. | |
| 2002/0137893 A1 | 9/2002 | Burton et al. | |
| 2002/0160360 A1 | 10/2002 | Chenchik et al. | |
| 2002/0167161 A1 | 11/2002 | Butland | |
| 2002/0129251 A1 | 12/2002 | Itakura | |
| 2002/0187263 A1 | 12/2002 | Sheu et al. | |
| 2003/0096273 A1 | 5/2003 | Gagna | |
| 2003/0142704 A1 | 7/2003 | Lawandy | |
| 2003/0142713 A1 | 7/2003 | Lawandy | |
| 2003/0162296 A1 | 8/2003 | Lawandy | |
| 2003/0177095 A1 | 9/2003 | Zorab et al. | |
| 2004/0063117 A1 | 4/2004 | Rancien et al. | |
| 2004/0166520 A1 | 8/2004 | Connolly | |
| 2004/0219287 A1 | 11/2004 | Regan et al. | |
| 2004/0219533 A1* | 11/2004 | Davis | C12Q 1/6813 435/6.19 |
| 2005/0059059 A1 | 3/2005 | Liang | |
| 2005/0112610 A1 | 5/2005 | Lee et al. | |
| 2005/0214532 A1 | 9/2005 | Kosak et al. | |
| 2006/0017957 A1 | 1/2006 | Degott et al. | |
| 2006/0017959 A1 | 1/2006 | Downer et al. | |
| 2006/0117465 A1 | 6/2006 | Willows et al. | |
| 2006/0121181 A1 | 6/2006 | Sleat et al. | |
| 2006/0286569 A1 | 12/2006 | Bar-Or et al. | |
| 2007/0012784 A1 | 1/2007 | Mercolino | |
| 2007/0048761 A1 | 3/2007 | Reep et al. | |
| 2007/0072197 A1 | 3/2007 | Rayms-Keller et al. | |
| 2007/0117119 A1 | 5/2007 | Akita et al. | |
| 2007/0254292 A1 | 11/2007 | Fukasawa | |
| 2008/0081357 A1 | 4/2008 | Kwon et al. | |
| 2008/0153135 A1 | 6/2008 | Liu | |
| 2008/0216255 A1 | 9/2008 | Poovey et al. | |
| 2008/0293052 A1 | 11/2008 | Liang et al. | |
| 2009/0075261 A1 | 3/2009 | Hayward et al. | |
| 2009/0136163 A1 | 5/2009 | Kerr | |
| 2009/0253127 A1 | 10/2009 | Gaudreau et al. | |
| 2009/0286250 A1 | 11/2009 | Hayward et al. | |
| 2009/0069199 A1 | 12/2009 | Brandenburg | |
| 2009/0311555 A1 | 12/2009 | Badyal et al. | |
| 2010/0050344 A1 | 3/2010 | Peltz et al. | |
| 2010/0075407 A1 | 3/2010 | Duffy et al. | |
| 2010/0285447 A1 | 11/2010 | Walsh | |
| 2010/0285490 A1 | 11/2010 | Dees et al. | |
| 2010/0285985 A1 | 11/2010 | Liang et al. | |
| 2011/0229881 A1 | 9/2011 | Oshima | |
| 2011/0250594 A1 | 10/2011 | Liang et al. | |
| 2013/0048731 A1 | 2/2013 | Flickner et al. | |
| 2014/0256881 A1 | 9/2014 | Berrada et al. | |
| 2014/0272097 A1 | 9/2014 | Jung et al. | |
| 2015/0018538 A1 | 1/2015 | Berrada et al. | |

FOREIGN PATENT DOCUMENTS

| | | |
|---|---|---|
| EP | 0 623 658 A2 | 11/1994 |
| EP | 0840350 A2 | 5/1998 |
| EP | 140333 A1 | 3/2004 |
| EP | 2444136 | 4/2012 |
| EP | 2444546 A | 4/2012 |
| GB | 702064 A | 1/1954 |
| GB | 2434570 A1 | 8/2007 |
| RU | 2084535 C | 7/1997 |
| RU | 2170084 C1 | 7/2001 |
| WO | 8706383 A1 | 10/1987 |
| WO | 90/144441 A1 | 11/1990 |
| WO | 9506249 A1 | 3/1994 |
| WO | 9502702 A1 | 1/1995 |
| WO | 9806084 A1 | 2/1996 |
| WO | 9745539 A1 | 12/1997 |
| WO | 9959011 A1 | 11/1999 |
| WO | 0125002 A1 | 4/2001 |
| WO | 2001036676 | 5/2001 |
| WO | 0055609 A1 | 9/2001 |
| WO | 0199063 A1 | 12/2001 |
| WO | 02057548 A1 | 7/2002 |
| WO | 02084617 A1 | 10/2002 |
| WO | 03030129 A2 | 4/2003 |
| WO | 30/080931 A1 | 10/2003 |
| WO | 2004025562 A1 | 3/2004 |
| WO | 2007078833 A | 7/2007 |

(56) References Cited

FOREIGN PATENT DOCUMENTS

| WO | 2008154931 A | 12/2008 |
|---|---|---|
| WO | 100075858 A1 | 3/2010 |
| WO | 2013170009 A1 | 11/2013 |

OTHER PUBLICATIONS

Supplementary European Search Report dated Mar. 28, 2018.
S. Hou, X. Li and X-Z Feng Method to improve DNA Condesation Efficiency by Alkali Treatment. Nucleosides, Nucleotides and Nucleic Acids, 2009. 28:725-735.Taylor & Francis Group, LLC.
M. Ageno, E. Dore and C. Frontali The Alkaline Denaturation of DNA, Biophys. J. Nov. 1969, 9(11): 1281. Abstract.
M. Ageno, E. Dore and C. Frontali The Alkaline Denaturation of DNA, Biophys. J. Nov. 1969, 9(11): 1281-1311.
T. Thiel, L. Liczkowski and S.T. Bissen New zwitterionic butanesulfonic acids that extend the alkaline range of four families of good buffers: Evaluation for use in biological Systems. J. Biochem. Biophys. Methods (1998) 37: 117-129. Elsevier.
Versalift, "Market Growth, the evolution of the aerial lift industry," Oct. 1, 2002. Accessed on web Nov. 10, 2008.
Schulz et al., "Archived or directly swabbed latent fingerprints as a DNA source for STR typing," Forensic Science International, 127 (2002) 128-130.
Zuckermann, et al. "Efficient methods for attachment of thiol specific probes to the 3' end of synthetic oligonucleotides." Nucleic Acids Research, vol. 15, pp. 5305-5321 (1987) IRL Press Limited, Oxford.
Whitcombe, et al. "Detection of PCR products using self-probing amplicons and fluorescence," Nature Biotechnology, vol. 17 pp. 804-807 (1999) Nature America, Inc. New York.
Tyagi, et al. Multicolor molecular beacons for allele discrimination, Nature Biotechnology, vol. 16, pp. 49-53 (1998) Nature Publishing Group, New York.
Nazarenko, et al. "A closed tube format for amplification and detection of DNA based on energy transfer," Nucleic Acids Research, vol. 25, pp. 2516-2521 (1997) Oxford University Press.
Tyagi & Kramer, "Molecular Beacons: Probes that Fluoresce upon Hybridization" nature Biotechnology, vol. 14, pp. 303-308 (1996) Nature Publishing Group, New York.
Sproat, et al. "The synthesis of protected 5'-mercapto-2',5'-didoexyribonucleoside-3-O-phosphoramidites, uses of 5'-nercapto-didoexyribonucleosides." Nucleic Acids Research, vol. 15, pp. 4837-4848 (1987) IRL Press Limited, Oxford.
Nelson, "Bifunctional oligonucleotide probes synthesized using a novel CPG support are able to detect single base pair mutations." Nucleic Acids Research, vol. 17, pp. 7187-7194 (1989) IRL Press Limited, Oxford.
Gupta, et al. "A general method for the synthesis of 3'-sulfhydryl and phosphate group containing oligonucleotides." Nucleic Acids Research, vol. 19, pp. 3019-3025 (1991) Oxford University Press, Oxford, England.
Lee, et al. "Allelic discrimination by nick translation PCR with fluorescent probes." Nucleic Acids Research, vol. 21, pp. 3761-3766 (1993) Oxford University Press, Oxford, England.
Holland, et al. "Detection of specific polymerase chain reaction product by utilizing the 5' [to] 3' exonuclease activity of Thermus aquaticus DNA polymerase." Proceedings of the National Academy of Sciences, USA vol. 86 pp. 7276-7280 (1991) National Academy of Sciences, Washington, DC.
Heid, et al. "Real Time Quantitative PCR." Genome Research, vol. 6, pp. 986-994 (1996) Cold Spring Harbor Laboratory Press, Woodbury, New York.
Gibson, et al. "A Novel Method for Real Time Quantitative RT-PCR" Genome Research, vol. 6, pp. 995-1001 (1996) Cold Spring Harbor Laboratory Press, Woodbury, New York.
Agrawal & Tang, "Site-specific functionalization of oligodoexynucleotides for non-radioactive labelling." Tetrahedron Letters, vol. 31, pp. 1543-1546 (1990) Pergamon Press, Great Britain.
Van Der Rijke, et al. "Up-converting phosphor reporters for nucleic acid microarrays." Nature Biotechnology, vol. 19, pp. 273-276 (2001) Nature Publishing Group, New York.
Corstjens, et al. "Infrared Up-converting phosphors for bioassays." IEE Proceedings-Nanobiotechnology, vol. 152, pp. 64-72 (2005) Institution of Engineering and Technology, London.
Hussein et al. "Molecular Characterization of Cotton Genotypes Using PCR-based Markers." Journal of Applied Sciences Research 3(10) 1156-1169 (2007). INSInet Publication.
Jiang, et al. "Polyploid formatioopn created unique avenues for response to selection in Gossypium (cotton)" Proceedings of the National Academy of Sciences, USA vol. 95 pp. 4419-4424 (1998) National Academy of Sciences, Nashington, DC.
Lee, et al. "The complete genome sequence of Gossypium hursutum, organization and phylogenetic relationships to other angiosperms." BMC Genomics 7:61, Mar. 2006.
Ibrahim, et al. Complete nucleotide sequence of the cotton (Gossypium barbadense L.) chloroplast genome with a comparative analysis of sequence among 9 dicot plants. Genes and Genetic Systems vol. 81. pp. 311-321 (2006).
Kaneda, S. et al. Modification of the glass surface property in PDMS-glass hybrid microfluidoc deuces. Analytical Sciences, Jan. 2012, vol. 28, No. 1, pp. 39-44.
Hosokawa, K. et al. DNA Detection on a power-free microchip with laminar flow-assisted dendritic amplification. Analytical Sciences, 2010, Vo. 26, No. 10, pp. 1052-1057.
Park, H. et al. Stress response of fibroblasts adherent to the surface of plasma-treated poly(lactic-co-glucolic acid) nanofiber matrices. Colloids surf B Biointerfaces, May 2010, 1; 77(1):90-95.
Tuzlakoglu K. et al. A new route to produce starch-based fiber mesh scaffolds by wet spinning and subsequent surface modification as a way to improve cell attachment and proliferation. J Biomed Mater Res A, Jan. 2010, 92 (1):369-377.
Karahan et al., Fibers and Polymers, vol. 9, pp. 21-26 (2008).
Ullrich, T. et al. Competitive reporter monitored amplification (CMA)-quantification of molecular targets by real time monitoring of competitive reporter hybridization. PLoS One, 2012, vol. 7, No. 4 E35438. doi;10.1371/journal.pone.0035438, p. 1-13.
Beija, Mariana; et al. Synthesis and applications of Rhodamine derivatives as fluorescent probes (2009) Critical Reviews, vol. 38: pp. 2410-2433. Chemical Society Reviews; Advance article published on the web Apr. 27, 2009.
Yang, X.F. et al. Fluorometric determination of hemoglobin using spiro form rhodamine B hydrazide in a micellar medium, Tantala, vol. 62(4):439-445; Nov. 12, 2003.
Instant Krazy Glue, product description, accessed website Feb. 24, 2012, 4 pages.
"Virus" (Wikipedia.com, accessed Nov. 24, 2012).
"How many species of bacteria are there" (wisegeek.com; accessed Jan. 21, 2014).
"Fungi" (Wikipedia.com; accessed Jun. 3, 2013).
"List of sequenced bacterial genomes" (Wikipedia.com; accessed Jan. 24, 2014).
"Fish" (Wikipedia.com; accessed Nov. 2, 2014).
"Mammal" (Wikipedia.com; accessed Sep. 22, 2011).
"Murinae" (Wikipedia.com; accessed Sep. 22, 2011).
"Plant" (Wikipedia.com; accessed Mar. 8, 2013).

* cited by examiner

METHOD AND DEVICE FOR MARKING FIBROUS MATERIALS

TECHNICAL FIELD

The invention pertains to a method and device for marking fibrous materials, such as cotton, and more particularly to a method and device for marking cotton and cotton products such as yarn and textiles as well as articles that include cotton, with a nucleic acid marker to identify and authenticate the article's origin and authenticity.

BACKGROUND

Cotton is an essential cash crop throughout the world. Many parts of the cotton plant are useful; however, cotton is particularly important in forming a variety of goods, for example, fabrics, clothing and many household items such as towels and tablecloths, etc. The use of cotton to generate fabric begins with processing of bales of cotton to liberate cotton fibers. Bales of cotton are typically opened by automated machinery to remove unprocessed lint. The lint can then be further cleaned by, for example, using a blower to separate short components of the lint from cotton fibers. The cotton fibers can then be woven into longer strands sometimes referred to as cotton yarn. The woven cotton fibers are useful in the manufacture of many different items, for example, fabrics, clothing and household items.

A single pound of cotton may yield many millions of cotton fibers. However, the lengths of individual cotton fibers vary according to the species or cultivars of the cotton plant from which the fibers originated. The quality of fabrics produced from cotton fibers vary according to the length of the individual cotton fibers. Relatively short cotton fibers are commonly harvested, for example, from the cotton species *G. hirsutum*, *G. herbaceum*, and *G. arboreum*. The relatively short fibers are generally considered of lower quality than longer cotton fibers harvested from the cotton species *G. barbadense*. *G. barbadense*-derived cotton fibers are commonly referred to as Extra Long Staple (ELS) cotton. ELS cotton is generally considered to produce higher quality and higher value fabrics, clothing, household items, and related products. Types of ELS cotton include, for example, American Pima, Egyptian, and Indian Suvin. Products carrying an ELS label, such as the aforementioned, American Pima, Egyptian, Supima, or Indian Suvin labels will generally command a higher price than products lacking such a designation.

Variability in cotton quality has lead to concerns over the authenticity of and accurate identification of quality cotton products. Once raw cotton or products containing cotton enter into the stream of commerce, which may include worldwide trade, it is often difficult to reliably determine whether cotton advertised as ELS cotton is, in fact, authentic or is blended or is composed entirely of short fiber cotton. It also may be difficult to determine whether a particular cotton product originated from a particular location, region or manufacturer. For example, counterfeit products manufactured from short fiber cotton may be inappropriately or fraudulently labeled as ELS, American Pima, Egyptian, or Indian Suvin cotton. Cotton products may also be fraudulently labeled as originating from a particular region of the world (e.g., as Egyptian cotton). There is an unmet need for a method of determining whether a particular article of cotton is entirely composed of authentic ELS cotton, or is a counterfeit article that includes significant amounts of or is in fact entirely composed of short staple cotton.

Counterfeiting and blending of high-end products with cheaper material has become a major liability problem for major brand names. The International Chamber of Commerce (ICC) reported that in 2008, counterfeited goods resulted in a loss of $650 billion in revenues and 2.5 million jobs. The ICC projected that the loss in revenues will exceed $1.7 trillion in 2015, which is equivalent to 2% of the world economy. In addition to the revenue losses, certain counterfeit products were linked directly to serious health and safety issues. The counterfeit goods have infiltrated most industries from textiles to microchips, and even pharmaceuticals.

SUMMARY

Exemplary embodiments of the present invention provide a method for marking fibrous materials, such as cotton, or an article that includes a fibrous material. The method includes depositing a solution comprising a nucleic acid marker onto at least a portion of the fibrous material. The deposition may be performed with a delivery mechanism comprising one or more outlets. The nucleic acid marker may be activated, for example, by adding a functional group to the nucleic acid marker.

In accordance with an exemplary embodiment of the invention, the nucleic acid marker may include DNA. In another exemplary embodiment, the DNA may be alkaline activated. In another exemplary embodiment, an amount of the solution comprising the nucleic acid marker deposited on the fibrous material or article manufactured from the marked fibrous material may be regulated, such as for instance, by a metering control.

In another exemplary embodiment, the marked fibrous material may include a material, such as for instance, a textile, a fiber, cotton, ginned cotton, a cotton blend, wool, yarn, nylon, or cashmere. The marked fibrous material may include a synthetic fabric or a synthetic fabric blend including, for example, rayon, nylon, wool, or polyester. The polyester synthetic fiber may include homopolymers, copolymers, aliphatics and/or aromatics. The polyester synthetic fiber may include any suitable polyester, such as for instance, polyethylene, polypropylene, or polyethylene terephthalate to name a few, and may be blended with other fibers, such as cotton fibers.

In one embodiment the present invention provides a method of marking fibers, wherein the method includes: providing a plurality of fibers in a manufacturing process; depositing a marker solution onto at least a portion of the fibers in the manufacturing process, the depositing being performed with a delivery mechanism comprising one or more outlets; and thereby marking the fibers.

In another embodiment the invention provides an apparatus for marking fibers, the apparatus includes: a transport system adapted to transport fibers in a direction of a marker delivery apparatus positioned at a location along the transport system; wherein the marker delivery apparatus comprises one or more outlets, adapted to deposit a solution comprising the marker through the one or more outlets onto at least a portion of the fibers; and thereby marking the fibers.

In another embodiment the invention provides a method of authenticating a fibrous material including: providing a plurality of fibers; depositing a nucleic acid marker onto at least a portion of the fibers, the depositing being performed with a delivery mechanism comprising one or more outlets; thereby producing marked fibers; obtaining a sample of the marked fibers and assaying the sample of marked fibers for the presence of the nucleic acid marker; and thereby determining whether the fibrous material is authentic or counterfeit.

DETAILED DESCRIPTION

Figure 1:
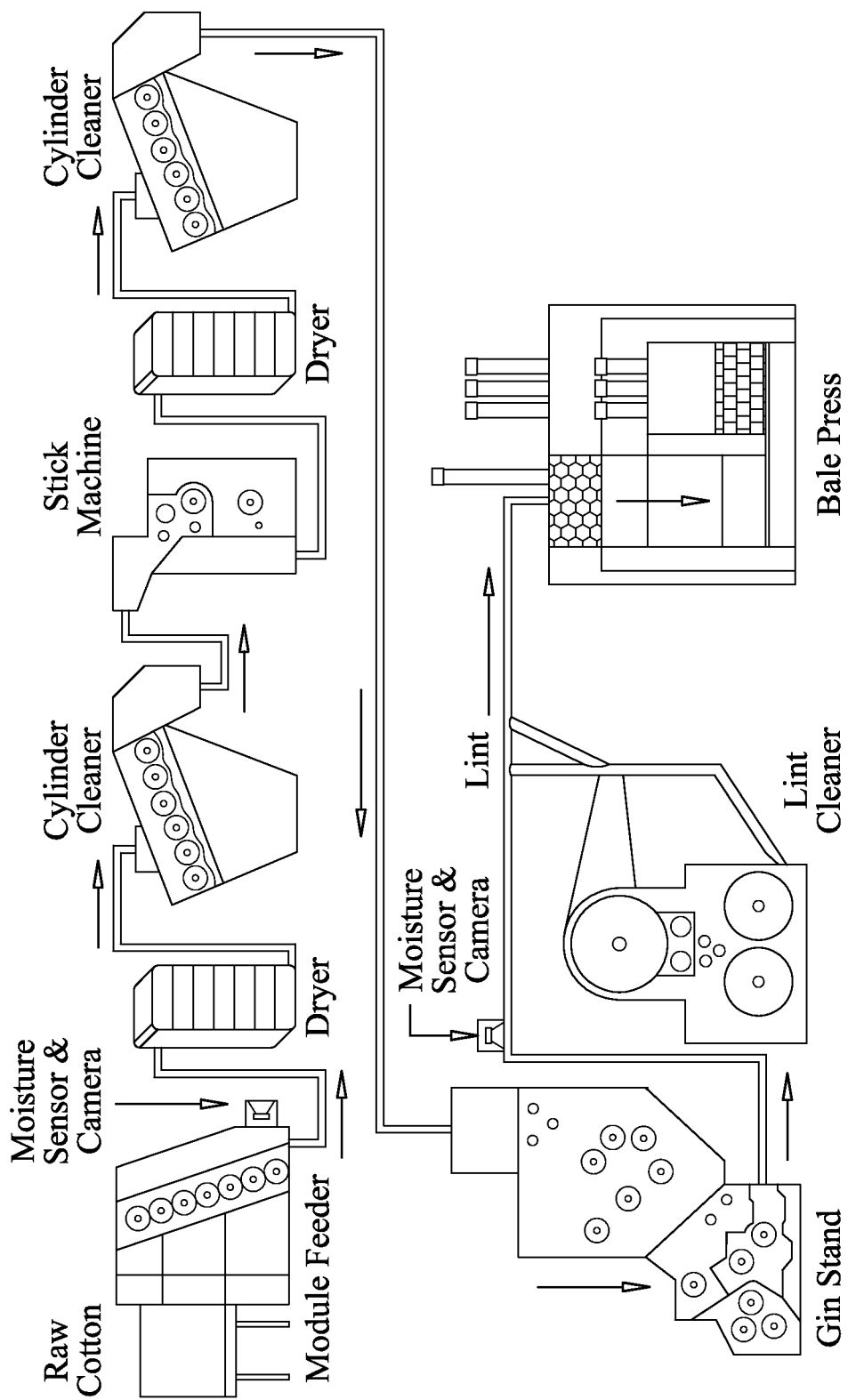
FIG. 1 shows a schematic of a cotton processing system. The raw cotton bale is opened and fed into the system through a feeder, passed through one or more serial dryers and cleaners and a stick machine to remove debris carried along with the cotton. The cotton is then processed through a cotton gin and lint cleaner before being pressed into standard sized 500 lb bales.

Exemplary embodiments of the present invention will be described below in more detail with reference to the accompanying drawings which should not be construed as limiting.

Exemplary embodiments of the present invention provide a method for marking an fibrous materials. The method includes depositing a solution comprising a nucleic acid marker onto at least a portion of the fibers. The deposition is performed with a delivery mechanism comprising one or more outlets. The nucleic acid marker may be activated, for example, by alkaline pre-treatment as described in US 2014/0256881, or by adding a reactive group to the nucleic acid marker.

Marker Molecules

In an exemplary embodiment of the present invention, a marker molecule to be deposited, linked, attached or bonded to the fibers or the article to be marked may be a biomolecule (e.g., a nucleic acid marker). The marker molecule may be an inorganic molecule and may include one or more metals, non-metals or rare earth metals. The biomolecule may be a protein, a peptide, a nucleic acid, a vitamin, or a protein-DNA complex. The nucleic acid may comprise, for example, RNA, DNA, an RNA-DNA complex, single stranded DNA or double stranded DNA. The nucleic acid may be any suitable size, for example, the nucleic acid may be in a range of about 50 base pairs to about 1000 base pairs. The nucleic acid may comprise any suitable natural or non-natural DNA sequence such as a synthetic DNA sequence that is not a natural DNA sequence. The non-natural DNA sequence may be formed by digesting and religating naturally or non-naturally occurring DNA. The DNA may be from any source, such as for instance, animal or plant DNA. The DNA may be derived from bacteria, viruses, fungi, or synthetic vectors or fragments or any combination thereof. The nucleic acid may comprise a non-naturally occurring DNA sequence formed by, for example, digesting and religating animal or plant DNA. The nucleic acid may include synthetic DNA, semi-synthetic DNA of a combination of synthetic and semi-synthetic DNA. The nucleic acid may comprise nuclear, mitochondrial or chloroplast DNA or total genomic DNA.

In an exemplary embodiment of the present invention, the nucleic acid marker may be derived from any suitable DNA source, such as for instance, DNA extracted from a plant source. The nucleic acid marker including DNA may interchangeably be referred to as a DNA taggant. The extracted DNA may be specifically or randomly digested and ligated to generate artificial nucleic acid sequences which are unique to the world. The digestion and ligation of the extracted DNA may be completed by standard restriction digestion and ligation techniques known to those skilled in the art of molecular biology. Digestion may be performed randomly or site-specifically, for example by random or site specific nucleases. The nucleic acid fragments resulting from digestions may be specifically or randomly rearranged to form new nucleic acid sequences (e.g., non-natural nucleic acid sequences). The sequence of the nucleic acid marker can be of any suitable length, for instance the sequence of the nucleic acid marker can be a sequence of from about 5 to about 5000 bases or a sequence from about 20 to about 1000 bases.

In an exemplary embodiment of the invention, the nucleic acid marker may include activated DNA, or any suitable functionalized DNA, for example, an alkaline pH activated DNA (see below). The method may include depositing the nucleic acid marker onto the surface of the fibers or article to be marked or into a liquid for binding, linking or attaching of the activated nucleic acid marker to the fibers or article, for example, onto a surface of the fibers or article or a portion of the surface of the fibers or article. The nucleic acid marker may be incorporated into the material or a portion of the material from which the article is formed. The alkaline pH activated nucleic acid marker including alkaline activated DNA may be bound to a material, such as, for instance, cotton, wool, nylon, plastic, metal, glass, wood, or printing ink. Alkaline activation of a nucleic acid marker is discussed in more detail below.

The term nucleic acid, which may be abbreviated as "NA" in the Figures, may refer to deoxyribonucleic acid (DNA) or ribonucleic acid (RNA). Nucleic acid markers may include nucleic acids from animals, plants, bacteria, viruses, fungi, or synthetic vectors or fragments or any combination thereof. The nucleic acid marker may be any suitable nucleic acid, such as for instance, a synthetic non-natural DNA, a semi-synthetic DNA derived from natural and synthetic sequences or a rearranged natural DNA sequence derived by cleavage and ligation of the cleavage fragments in a new non-natural sequence.

The nucleic acid marker may have a specific template sequence and/or a specific template length, so that when polymerase chain reaction (PCR) procedures are performed, PCR primers may be any specific primer pairs with a complementary nucleic acid sequence which can bind nucleic acids of the nucleic acid marker template. There may be a relatively low concentration of nucleic acids in the nucleic acid marker and the nucleic acids may be amplified by techniques well known to those skilled in the art of molecular biology.

The nucleic acid marker may be mixed into solution with water or any desired aqueous solution or buffer to form the solution comprising the nucleic acid marker for use in the methods of the invention. For example, nucleic acids may be mixed with water to form the solution comprising the nucleic acid marker. The solution comprising the nucleic acid marker may be mixed at any desired concentration to mark the fibers or article to be marked. For example, the concentration of nucleic acid to solvent may be approximately 1 attogram/milliliter ($10^{-18}$ g/ml), 1 femptogram/milliliter ($10^{-15}$ g/ml), 1 picogram/milliliter ($10^{-12}$ g/ml), 1 nanogram/milliliter ($10^{-9}$ g/ml) or 1 microgram/milliliter ($10^{-6}$ g/ml). Alternatively, the concentration of nucleic acid in the solution may be in a range from approximately 1 attogram/milliliter ($10^{-18}$ g/ml) to approximately 1 microgram/milliliter ($10^{-6}$ g/ml). The solution comprising the nucleic acid marker may include more than one nucleic acid marker.

It will also be appreciated by those of skill in the art that the nucleic acid marker may be combined with one or more optical reporters, for instance, an infrared marker. For example, the optical reporter may be chemically linked to the nucleic acid marker or the optical reporter may be mixed into the solution comprising the nucleic acid marker. The optical reporter may be, for instance, an upconverting phosphor or a fluorophore. The nucleic acid marker and the optical reporter can be mixed in a dying process. The combination or mixture of the nucleic acid marker and the optical reporter may be applied to one or more articles to be marked, such as for instance, fibers or fibrous materials. The fibers or fibrous materials may be materials suitable for being combined to form textiles. The marked fibers may then be blended with one or more unmarked fibers to generate a marked textile. The blending of the marked fibers with the unmarked fibers may be performed during ginning, before opening, during opening, before blending, or during blending. The fibers may be raw fibers, and may be marked during or after scouring. Raw fibers (e.g., raw cotton fibers or raw wool fibers) may refer to fibers that have been ginned, or ginned and scoured. For example, the raw fibers that have been separated from cotton plant material by ginning, but that have not yet been scoured may include small plant parts and foreign matter that is not removed by the ginning process.

Activation of Nucleic Acids

Nucleic acids (e.g., DNA) can be activated to enhance binding between the nucleic acid and the fibers or article to be marked by methods well known in the art (See for instance, G. T. Hermanson, *Bioconjugate Techniques*, 2d ed., 2008, Academic Press). Activating the nucleic acid may make the nucleic acid physically or chemically reactive with the surface of the fibers or article to be marked (e.g., by rendering the nucleic acid capable of ionically or covalently bonding to an available group on the surface of the article). For example, the nucleic acid may be activated by exposure to alkaline conditions. Alkaline activation of nucleic acids may be achieved as described in US2014/0256881.

A reactive functional group may be bound to the nucleic acid to facilitate binding between the nucleic acid and the fibers or the article to be marked. The reactive functional group may be bound to the nucleic acid through a process of alkaline activation of the DNA molecule (described in more detail below). The reactive functional group may be capable of covalently binding to an available group on at least a portion of the fibers or the article to be marked. The reactive functional group may immobilize the nucleic acid to the fibers or the article.

The nucleic acid may be bound to at least a portion of the surface of the fibers or the article to be marked by a chemical linker bound through a reactive functional group. For example, the chemical linker may include a chain of carbon atoms with a reactive functional group at an end of the chain of carbon atoms. The end of the chain of carbon atoms opposite to the reacting functional group may be covalently bound to the nucleic acid. The reactive functional group may be activated to covalently bind with an available group on the surface of the fibers or the article. Activation of the reactive functional group may be performed by exposure to alkaline conditions.

Generating a Solution Comprising a Nucleic Acid Marker for Textile Applications

The solution comprising the nucleic acid marker may be formed by mixing the nucleic acid in water. A concentrated solution of nucleic acid marker may be mixed with water to form the solution comprising the nucleic acid marker before the solution comprising the nucleic acid marker is deposited onto the fibers or the article. The nucleic acid marker may be alkaline activated. For example, the nucleic acid marker may be exposed to the alkaline conditions discussed in detail above. An alkaline activator may be provided and the alkaline activator may be mixed with the solution comprising the nucleic acid marker to form an activated nucleic acid marker. The solution comprising the nucleic acid marker may be an aqueous solution comprising the nucleic acid marker. The solution comprising the nucleic acid marker may comprise any suitable working solution, such as an aqueous solution, which may include a buffer.

In an exemplary embodiment of the present invention, the solution comprising the nucleic acid marker may comprise a non aqueous solvent (e.g., polyurethane or silicone). The solution comprising the nucleic acid marker and the working solution may be mixed to form the solution comprising the nucleic acid marker according to the methods described in U.S. Pat. No. 7,115,301. The solution comprising the nucleic acid marker may be generated by mixing the nucleic acid marker with a media that causes the nucleic acid marker to adhere to a fibrous material. For example, the nucleic acid marker may be mixed with water. The solution comprising the nucleic acid marker is then applied to the fibers or the article to be marked, for example, a textile material such as a fiber or a fibrous material. As a result of this application, a marked fibrous material may be generated by causing the nucleic acid marker to adhere to the fibrous material. By way of example and not of limitation, the media may include an aqueous solvent, an adhesive, a polymer, a binder, or a cross-linking agent. The media may include an acrylic, polyurethane, dimethoyldihydroxyethyleneurea, polyvinyl alcohol, a starch, an epoxy, or polyvinyl chloride.

According to an exemplary embodiment of the invention, a media may be selected that is used as a topical treatment for a fibrous material. The media may be mixed with the nucleic acid marker to generate the solution comprising the nucleic acid marker suitable for topical treatment of the fibers or the article. The solution comprising the nucleic acid marker may then be topically applied to the article (e.g., a fibrous material). The marked fibrous material may be generated by causing the nucleic acid marker to adhere to the fibrous material. The media suitable for topical treatment may include colorants, dyes, dyeing auxiliaries, print pastes, softeners, lubricants, antistatic agents, water repellants, antimicrobial agents, wetting agents, leveling agents, or water.

According to an exemplary embodiment of the invention, the media may be a viscous spinning solution for fiber spinning. The viscous spinning solution may be mixed with the nucleic acid marker to generate a viscous dope including the nucleic acid marker. The viscous dope may then be extruded through an opening in a spinneret to form the marked fiber. The marked fiber may then be solidified and can then be used at any stage in the textile manufacturing process, for example during the washing, scouring, ginning, carding, combing, roving, spinning, reeling, winding, sizing, bundling, spooling, weaving, knitting or finishing stage of the textile manufacturing process.

According to this exemplary method the solution comprising the nucleic acid marker may be embedded in the fiber.

According to an exemplary embodiment of the invention, the nucleic acid may be mixed with a water insoluble media to generate the solution comprising the nucleic acid marker. Firstly, the nucleic acid may be dissolved in a water soluble solution. The method then proceeds to dissolve the water insoluble media in a solvent. An intermediate solution is then used to mix the water soluble solution having the nucleic acid marker with the water insoluble media. The resulting solution comprising the nucleic acid marker is then applied to the desired fibers or article. By way of example and not of limitation, the intermediate solution used to generate the solution comprising the nucleic acid marker may include an organic solvent such as ethanol, acetone, chloroform or other such organic mixtures.

The solution comprising the nucleic acid marker may be deposited onto a textile fibers or the article during a textile manufacturing process. There are a number of insertion points in the textile manufacturing process that can be used for depositing the solution comprising the nucleic acid marker onto a textile material. For example, the solution comprising the nucleic acid marker may be applied to a textile material during or after a scouring or ginning process (discussed below in more detail with reference to FIG. 2). A plurality of insertion points in the textile manufacturing process are described in further detail below.

Application of the Nucleic Acid Marker to Fibers or an Article

In exemplary embodiments of the invention, the fibers or article may include a textile, a fiber, cotton, raw cotton, ginned cotton, a cotton blend, wool, yarn, cashmere, a synthetic fabric and a synthetic fabric blend. The fibers/article may be, for example, any natural material, fabric or raw material capable of being treated with the solution comprising the nucleic acid marker. The solution comprising the nucleic acid marker may be applied to fibers, yarns, sewing thread, fabrics, non-woven materials, and any product made from fibrous materials, such as a textile including wool or cotton fibers. The article may be any consumer product capable of being treated with the solution comprising the nucleic acid marker.

In an exemplary embodiment, the solution comprising the nucleic acid marker may be dried onto the fibers or the article to be marked or absorbed into a material used to make the article. For example, the fibers/article may be a textile article including cotton or wool and the solution comprising the nucleic acid marker may be dried on a textile article. The solution comprising the nucleic acid marker may be dried by any suitable drying process, for example, air drying, oven drying, IR drying, or UV curing. Fibers may be any substance, natural or manufactured, with a high length-to-width ratio and with suitable characteristics for being processed into fabric in which the smallest component is hair-like in nature and can be separated from a fabric. Natural fibers may be those that are in a fiber form as they grow or develop and may be from animal, plant, or mineral sources, for example. Manufactured fibers (e.g., synthetic fibers) may be made from chemical compounds produced in manufacturing facilities. The manufactured fiber may be, for instance, Rayon or nylon.

Yarns may be an assemblage of fibers that are twisted or laid together so as to form a continuous strand that can be made into a textile fabric or a textile article. A yarn may be a continuous strand of textile fibers, filaments, or materials in a form suitable for knitting, weaving, or otherwise intertwining to form a textile fabric. Filament yarns may be made from manufactured fibers, except for a relatively small percentage that is filament silk. Manufactured filament yarns may be made by extruding a polymer solution through a spinneret, solidifying it in fiber form, and then bringing the individual filaments together with or without a twist. Spun yarns may be continuous strands of staple fibers held together by a mechanism such as a mechanical twist that uses fiber irregularities and natural cohesiveness to bind the fibers together into one yarn.

Sewing thread may be a yarn intended for stitching materials together using machine or hand processes. Fabric may be a flexible planar material constructed from solutions, fibers, yarns, or fabrics, in any combination. A fabric may be a pliable, flat structure that can be made into two- or three-dimensional products that require some shaping and flexibility. Fabrics can be made from a wide variety of starting materials, such as for instance, solutions, fibers, yarns, "composite" fabrics, fiberglass or carbon fiber. For fabrics made from yarns, the fabric may be a woven or knitted fabric. Woven fabrics may be made with two or more sets of yarns interlaced at right angles. Knitting is a process which may form a fabric by the interlooping of one or more sets of yarns. Fabrics from solutions may include films in which the films are made directly from a polymer solution by melt extrusion or by casting the solution onto a hot drum. Composite fabrics are fabrics that combine several primary and/or secondary structures, at least one of which may be a recognized textile structure, into a single structure. Some fabrics may be made directly from fibers or fiber forming solutions without processing of fibers into a yarn. These nonwoven structures may include textile-sheet structures made from fibrous webs, bonded by mechanical entanglement of the fibers or by the use of added resins, thermal fusion, or formation of chemical complexes.

Those skilled in the art shall appreciate that the systems and methods described above may be used to mark fibers or articles, such as for instance, packaging materials, labeling materials, documents, and shipping containers for determining the origin, authenticity, or other supply chain or product information.

Figure 3:
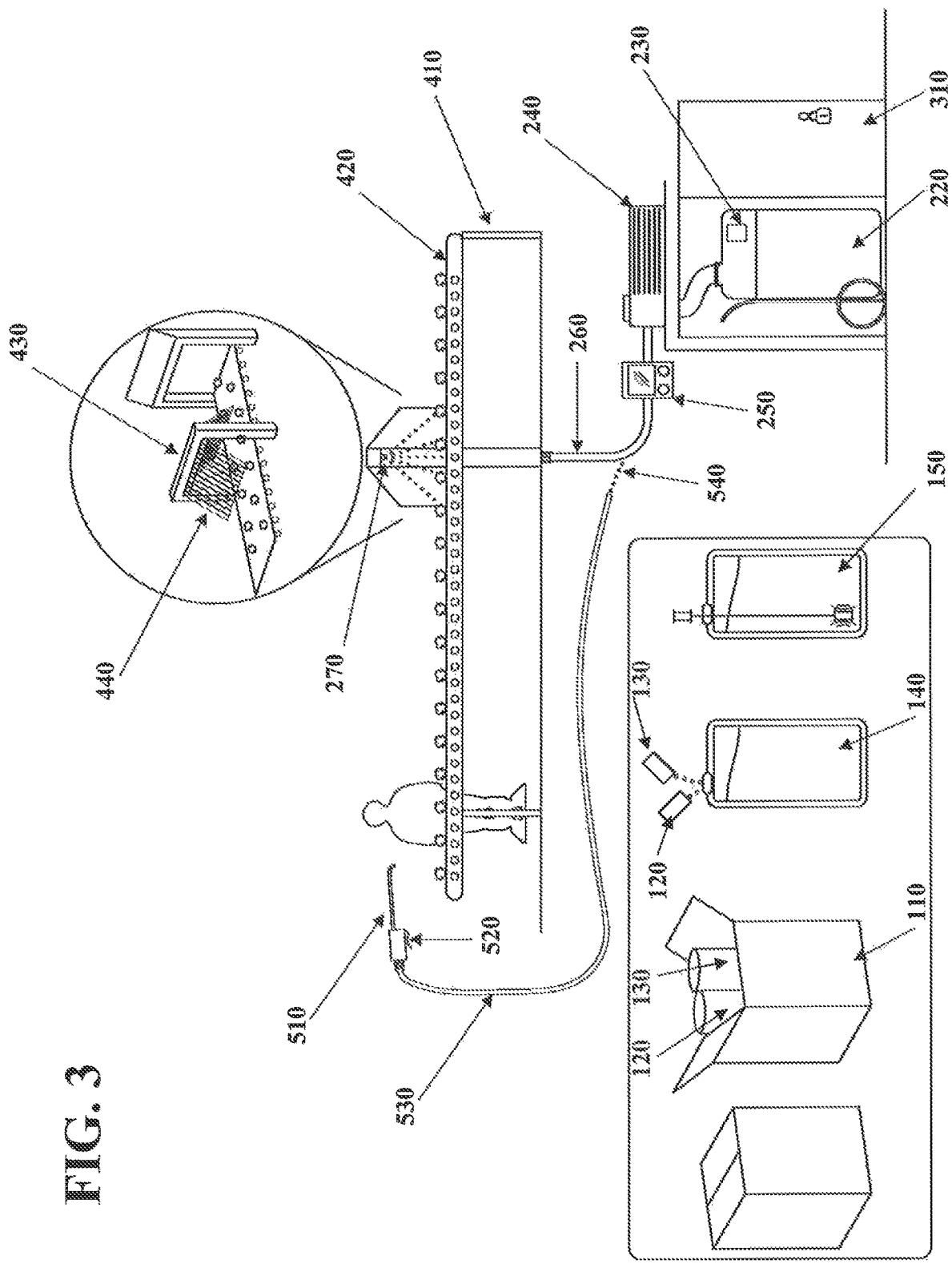
FIG. 3 illustrates a method for depositing a nucleic acid marker onto an article or fibrous material and a device configured to apply the method of depositing the nucleic acid marker thereon according to exemplary embodiments of the present invention.

In exemplary embodiments of the invention, fibers or an article marked by a process is provided. The process may include providing the fibers/article and placing the fibers/article on any suitable surface to be held for deposition of the solution comprising the nucleic acid marker. For example, the article may be placed on a substrate, a surface, such as a platform, which may be a moving platform, or a conveyor belt. The method of marking the fibers or article may include conveying the article along the conveyor belt in the direction of the delivery mechanism positioned at a location along the conveyor belt. The delivery mechanism may comprise one or more outlets. The method of marking the fibers or article may include depositing the solution comprising the nucleic acid marker onto the fibers or article through the one or more outlets of the delivery mechanism and thereby marking the article. Exemplary apparatuses for marking the fibers or article are described below in more detail with reference to FIGS. 3 and 4.

In one exemplary embodiment, the textile manufacturing process may have a variety of insertion points for the nucleic acid marker. The nucleic acid marker may be applied to the processed or unprocessed fibers or to a textile at any point during the manufacturing process for a textile (e.g., to a raw textile material such as raw wool or raw cotton), or to a textile at any point in the stream of commerce (e.g., a finished textile article passing through the stream of commerce). The nucleic acid marker may be applied as the solution comprising the nucleic acid marker as described above. The insertion points for the solution comprising the nucleic acid marker provide for the application of the solution comprising the nucleic acid marker during the illustrative textile manufacturing process. During the textile manufacturing process, one or more solutions comprising the nucleic acid marker may be inserted at one or more insertion points of the manufacturing process. A database may be maintained to store information regarding each of the nucleic acid sequences for each manufacturer or process using the textile manufacturing process.

One exemplary insertion point is after the bowling or opening and picking process. The illustrative method then proceeds to the process steps of carding during which staple fibers are drawn together in a somewhat parallel arrangement to form a relatively weak rope of fibers. The method continues to combing which is an additional step in the production of smooth, fine, uniform spun yarns made of long-staple fibers. The next step is drawing in which a manufactured fiber may be elongated after spinning to alter the molecular arrangement within the fiber. During roving, the elongated fiber may be reduced in size, fibers may be made more parallel, and a relatively small amount of twisting may be introduced.

A second illustrative insertion point for the solution comprising the nucleic acid marker is after the roving process and before spinning. Spinning may refer to a process of producing yarn from raw or staple fibers. Spinning may also refer to the production of a fiber by extruding a solution through small holes in a spinneret.

A third illustrative insertion point is after spinning. The following steps may be performed to form an original cotton cloth. Forming the original cotton cloth may include the steps of conditioning, winding, singeing, doubling, singeing, reeling, mercerizing, bounding and/or baling. Winding refers to a process of transferring yarn from one package to another. Singeing refers to a process of burning fiber ends to produce a smooth surface. Reeling refers to a process of removing fibers and winding the removed fibers into a reel. Mercerization refers to a finishing process in which sodium hydroxide is used to increase cotton's absorbency, luster and/or strength. After the original cotton cloth is generated, the method proceeds to a step in which a basic/high temperature treatment may be performed to remove, proteins, wax, lipids and other impurities.

An illustrative fourth insertion point occurs after the high temperature treatment and before dying. The dyeing process may refer to the addition of color to the illustrative textile manufacturing process. Textiles may be produced by the use of dye or pigment mixtures. Pigments may include insoluble color particles that may be held on the surface of fabric by a binding agent. Dye may be an organic compound composed of a colored portion and may include a site that permits bonding to the fiber. Thus, for the illustrative fourth insertion point the nucleic acid marker may be combined with a dye mixture or pigment mixture prior to attachment of the nucleic acid market to the textile.

After dyeing, the method proceeds to knitting. Knitting may refer to the process of fabric production by interlooping yarns. A illustrative fifth insertion point occurs after knitting and before cloth dyeing. A illustrative sixth insertion point occurs after cloth dyeing. In the illustrative textile manufacturing process, the cloth dyeing process may be performed after knitting so that the knitted textile may be colored again. The nucleic acid marker may be combined with a dye mixture or pigment mixture prior to deposition on the textile. During the above-listed first three insertion points, the solution comprising the nucleic acid marker may be deposited directly onto a fiber or a fibrous material. As described above, the nucleic acid marker may be combined with a media that generates the solution comprising the nucleic acid marker that will cause the nucleic marker to adhere to the fibrous material or to products made from fibrous materials. The media may cause the nucleic acid marker to adhere to the fibrous material or to products made from fibrous materials. For example, the media may include an alkaline activator.

At the fourth and fifth insertion points the nucleic acid marker may be deposited during "finishing" processes. A finishing process may be a process used to add color and augment performance of unfinished fabric. A finish may be a process that is performed, for example, on fiber, yarn, or fabric either before or after fabrication to change the appearance, the texture or feel, or the performance of the marked fibers or the marked article.

The method for generating the solution comprising the nucleic acid marker for deposition onto the textile article in the textile manufacturing process may be performed in a variety of different ways. According to an exemplary embodiment, forming the solution comprising the nucleic acid marker may include the step of mixing the unique nucleic acid sequence with a first media that is liquefied in a solvent. The solution comprising the nucleic acid marker may then be applied to the textile. The first media may solidify after the evaporation of the solvent component of the solution.

According to an exemplary embodiment of the present invention, the nucleic acid marker may be mixed with a water insoluble media to generate the solution comprising the nucleic acid marker. The nucleic acid may be first dissolved in a water soluble solution. Then the water insoluble media may be dissolved in a solvent. An intermediate solution may then be used to mix the water soluble solution having the nucleic acid marker with the water insoluble media. The resulting solution comprising the nucleic acid marker may then be applied to the textile.

According to an exemplary embodiment of the invention, a method to deposit the nucleic acid marker on the fibers/article may include activating the nucleic acid marker and/or activating at least a portion of the surface of the article onto which the nucleic acid marker is deposited. The nucleic acid marker alone may be activated, or the surface of the article may be activated or both the nucleic acid marker and the surface of the fibers/article may be activated. By way of example and not of limitation, an activated site on the nucleic acid marker may be generated which reacts with cellulose (cotton fiber, etc.). The activated site on the nucleic acid marker may also react with nylon, certain polyesters, wool, or other fiber types.

Figure 2:
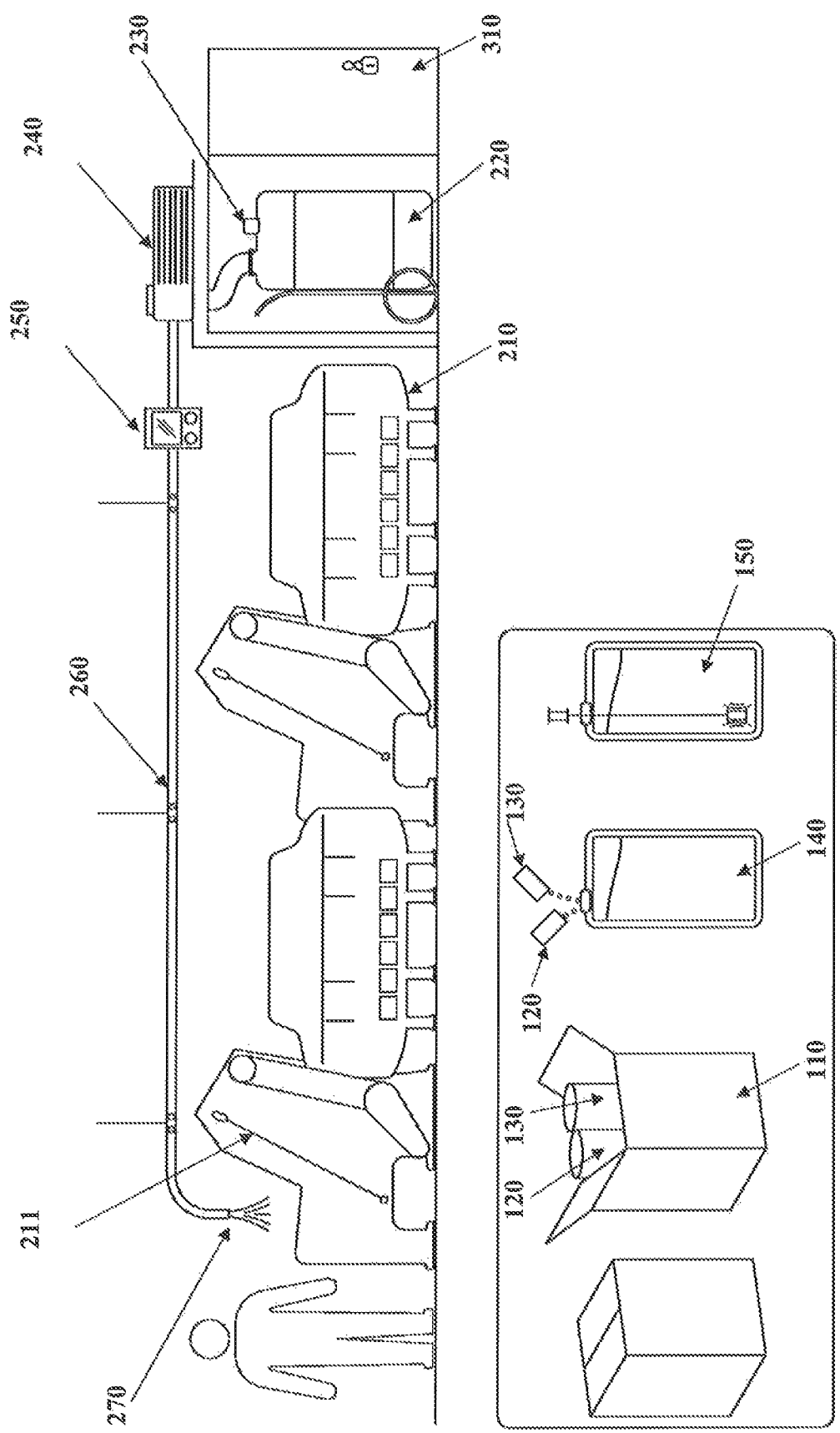
FIG. 2 illustrates a method for depositing a nucleic acid marker onto an article or fibrous material and a device configured to apply the method of depositing the nucleic acid marker thereon according to exemplary embodiments of the present invention.

FIG. 2 illustrates a method for depositing a nucleic acid marker onto fibers or onto an article and a device configured to apply the method of depositing the nucleic acid marker onto the article according to exemplary embodiments of the invention. With reference to FIG. 2, according to an exemplary embodiment of the present invention, the device for marking the article may be configured to apply the nucleic acid marker to a raw textile material (e.g., raw cotton fibers or raw wool fibers) during ginning by spraying the solution comprising the nucleic acid marker onto the raw textile material. The device for marking the textile article may be used in conjunction with an automated ginning machine including one or more conveyor belts 211 and one or more scouring bowls 210 connected in series and configured to scour the raw textile material. The device for marking the textile may be configured to apply the solution comprising the nucleic acid marker to the raw textile material during scouring of the raw textile material. The raw textile material may be any raw textile material, for example, raw wool or raw cotton.

The device for marking the textile may include a reservoir barrel 220 storing the solution comprising the nucleic acid marker, a pump 240, a metering control 250, a delivery mechanism 260 and one or more outlets 270. The device may include an indicator 230 operatively connected to the reservoir barrel 220 and configured to indicate when an amount of the solution comprising the nucleic acid marker in the reservoir barrel 220 is low. The reservoir barrel 220 may be stored in a lockable space 310 configured to record the time and identity of anyone accessing the lockable space.

The reservoir barrel 220 may be of any desired size or dimensions suitable for holding the desired amount of nucleic acid marker mixture. The size of the reservoir barrel 220 may be determined based on the amount of nucleic acid marker mixture desired to be held. For example, the size of the reservoir barrel 220 may be selected in order to continuously spray the solution comprising the nucleic acid marker onto the fibers or article for a desired period of time. The size of the reservoir barrel 220 may be determined based on the amount of raw textile material to be marked. For example, the reservoir barrel 220 may be any suitable size, such as for instance and without limitation, a 55 gallon barrel configured to store the solution comprising the nucleic acid marker.

The indicator 230 connected to the reservoir barrel 220 and configured to indicate when the amount of nucleic acid marker mixture in the reservoir barrel 220 is low may include a visual indicator, such as, for instance, a meter, an indicator, or a light. For example, a red light may indicate the amount of nucleic acid marker mixture is low and a green light may indicate the amount of nucleic acid marker mixture is not low. In another example, a yellow light may indicate an intermediate volume of nucleic acid marker mixture.

The pump 240 may be connected the reservoir barrel 220 and may be configured to pump the solution comprising the nucleic acid marker from the reservoir barrel 220 to the delivery mechanism 260. The pump 240 may have the capacity to pump any desired amount of the solution comprising the nucleic acid marker to the delivery mechanism 260. For example, an appropriately sized pump 240 may be selected based on a desired flow rate to deposit a particular amount of the solution comprising the nucleic acid marker on the raw textile material. For example, the pump 240 may be configured to deliver an amount of the solution comprising the nucleic acid marker to mark the raw textile material in an amount of 1 ng of DNA/kilogram of raw textile material to 1 µg of DNA/kilogram of raw textile material. The pump 240 may be configured to pump an amount of the solution comprising the nucleic acid marker to mark a raw textile material, such as for instance, raw cotton or raw wool.

Both wool and cotton have an inherent water content which contributes to the overall measured weight for processed cotton that is appropriate for textile production. During typical preparation procedures for cotton and wool, the final water content for processed cotton or wool is maintained at industry accepted levels. For example, the length and intensity of a drying process may increase or decrease the relative amount of water remaining in cotton or wool after it has been processed. The water content concentration of processed cotton that has not been marked with the solution comprising the nucleic acid marker may generally be maintained at approximately 8.5% w/w of water per total weight of cotton. The water content of processed wool that has not been marked with the solution comprising the nucleic acid marker may generally be maintained at approximately 12% w/w of water per total weight of wool. In order to mark raw textile materials such as cotton or wool with 2% w/w of the solution comprising the nucleic acid marker per total weight of raw textile material, the water content of cotton or wool may be reduced by approximately 2% w/w and may be replaced with approximately 2% w/w of the solution comprising the nucleic acid marker per total weight of raw textile material such that the standard 8.5% water content for cotton and 12% water content for wool, are maintained.

The flow rate of the pump 240 and/or a deposition rate of the delivery mechanism 260 may be controlled by any suitable means, such as for instance by a metering control unit 250. The metering control unit 250 may be positioned at any desired location. For example, the metering control unit 250 may be positioned adjacent to the pump 240 or near the one or more outlets 270 of the delivery mechanism 260. The metering control unit 250 may control the flow rate of the solution comprising the nucleic acid marker to or through the delivery mechanism 260. The metering control unit 250 may control the amount of the solution comprising the nucleic acid marker exiting each of the one or more outlets 270 of the delivery mechanism 260. Thus, the metering control unit 250 may control the deposition rate of the solution comprising the nucleic acid marker onto the raw textile material and may therefore control the amount of nucleic acid used to mark a particular raw textile material.

The delivery mechanism 260 may include one or more outlets 270. The one or more outlets 270 may be positioned at any location along the delivery mechanism 260. For example, the one or more outlets 260 may be positioned to discharge the solution comprising the nucleic acid marker as a mist over the raw textile material being conveyed through a ginning machine or scouring bowls 210. The scouring bowls 210 may carry the raw textile material to an elevated point along on or more angled conveyor belts 211 and allow the raw textile material to fall to a subsequent component of the scouring bowls 210. This process may be carried out as part of scouring or ginning the raw textile material. The one or more outlets 270 may be positioned to discharge the solution comprising the nucleic acid marker onto the raw textile material at the point where the raw textile material is allowed to fall to the subsequent scouring bowl 210.

According to exemplary embodiments of the invention, the nucleic acid marker solution may be pumped out of the reservoir barrel 220 and into the delivery mechanism 260. The nucleic acid marker solution may be pumped through the delivery mechanism 260 to the one or more outlets 270. The nucleic acid marker solution may then be sprayed onto the raw textile material through the one or more outlets 270.

According to an exemplary embodiment of the invention a concentrated nucleic acid marker 120 and an alkali activator 130 may be provided at step 110. The concentrated nucleic acid marker 120 and the alkali activator 130 may be added to water at step 140 and the resulting solution may be agitated at step 150 to form an activated solution comprising the nucleic acid marker. The activated solution comprising the nucleic acid marker may then be transferred to the reservoir barrel 220 for use. A pre-activated solution comprising the nucleic acid marker may also be provided in a reservoir barrel 220.

FIG. 3 illustrates a method for depositing a nucleic acid marker onto fibers or onto an article and a device configured to apply the method of depositing the nucleic acid marker onto the fibers/article according to exemplary embodiments of the invention. Except where otherwise indicated, the device and method illustrated in FIG. 3 are substantially the same or similar to the device and method discussed with reference to FIG. 2. With reference to FIG. 3, according to an exemplary embodiment of the invention, the device for marking the fibers/article may be configured to apply the solution comprising the nucleic acid marker onto the raw textile material during picking/cleaning of the raw textile material by spraying the solution comprising the nucleic acid marker onto the raw textile material. The device for marking the textile article may be used in conjunction with a picking/cleaning line machine 410 including one or more conveyor belts 420 and may be configured to allow picking/cleaning of the raw textile material. The device for marking the textile may be configured to apply the solution comprising the nucleic acid marker onto the raw textile material during picking/cleaning of the raw textile material. The raw textile material may be any raw textile material, for example, wool or cotton.

The delivery mechanism 260 may include one or more spray bars 430 holding the one or more outlets 270 of the delivery mechanism 260. The spray bars 430 may be suspended over the conveyor belt 420 of the picking/cleaning line machine 410. The spray bar 430 may include a shroud 440 configured to prevent the solution comprising the nucleic acid marker from being sprayed in an area outside of the conveyor belt 420. The shroud 440 may be of any desired size or dimensions suitable for preventing the solution comprising the nucleic acid marker from being sprayed in the area outside of the conveyor belt 420. For example, the shroud 420 may have a pyramid shape including two shielding elements extending at a downward angle from the spray bar.

According to an exemplary embodiment of the invention, the device may include a manual applicator 510 configured to be manually operated by a person positioned along the conveyor belt 420. The manual applicator 510 may include an on/off switch or a discharge lever 520 configured to activate the manual applicator 510. The manual applicator 510 may be configured to discharge the solution comprising the nucleic acid marker at any point along the conveyor belt 420. The manual applicator 510 may include a delivery hose 530 connected to the pump 240 and/or the metering control 250. The manual applicator 510 may include a quick disconnect component 540 configured to attach and/or release the delivery hose 530 of the manual applicator 510 to the pump 240 or the metering control 250. The manual applicator 510 may also be connected directly to the reservoir barrel 220 and may include its own pump and/or metering control.

An exemplary embodiment of the invention provides a device for marking fibers or an article including a conveyor belt adapted to convey an article in a direction of a delivery mechanism positioned at a location along the conveyor belt. The conveyor belt may be of any height, width, length or other desired dimensions to accommodate the article to be marked. The conveyor belt may be adapted to move in any desired direction. The conveyor belt may be motorized or manually operable. The conveyor belt may convey the article at a variety of speeds. The speed of the conveyor belt may be adjusted either manually or automatically. The conveyor belt may be controlled by a computer system. The conveyor belt speed may be adjusted according to, for example, a flow rate, a flow pressure or a deposition rate of the solution comprising the nucleic acid marker.

The delivery mechanism may include one or more outlets. The number of outlets may vary according to, for example, the amount of solution comprising the nucleic acid marker that is deposited on the fibers/article. The number of outlets may vary according to the size of the conveyor belt or the speed of the conveyor belt. The size of the one or more outlets may be individually and/or collectively adjustable in order to regulate, for example, the flow rate, flow pressure or a deposition rate of the solution comprising the nucleic acid marker. The position of the one or more outlets on the delivery mechanism may be adjustable so that the one or more outlets can be moved. The direction that the one or more outlets face may adjustable, for example, to adjust the direction that the solution comprising the nucleic acid marker exits the one or more outlets. The shape of the one or more outlets may be any suitable shape to output a solution comprising the nucleic acid marker. For example, the one or more outlets may be formed in a cone or cylinder shape. The one or more outlets may be adapted to provide a mist with the solution comprising the nucleic acid marker onto the material to be marked. The one or more outlets may be adapted to provide a continuous, non-continuous or intermittent spray onto the material to be marked.

The delivery mechanism may be adapted to deposit the solution comprising the nucleic acid marker through the one or more outlets onto the material and marking the material with the solution comprising the nucleic acid marker. The delivery mechanism may be positioned at any suitable region along the conveyor belt. For example, the delivery mechanism may cover a width of the conveyor belt. The delivery mechanism may be positioned at any desired angle to deposit the solution comprising the nucleic acid marker onto the material to be marked. For example, the delivery mechanism may be suspended above the conveyor belt or along the side of the conveyor belt. More than one delivery mechanism may be positioned at more than one location along the conveyor belt. The delivery mechanism may include one or more reservoirs, and the reservoirs may store the solution comprising the nucleic acid marker.

In an exemplary embodiment of the invention, the one or more outlets may be disposed on a spray bar positioned to deliver the solution comprising the nucleic acid marker onto the fibers/article. The spray bar may be adapted to deposit the solution comprising the nucleic acid marker through the one or more outlets onto the fibers/article and marking the fibers/article with the solution comprising the nucleic acid marker. The spray bar may be positioned at any region of the platform of the conveyor belt. The spray bar may be positioned at any desired angle to deposit the solution comprising the nucleic acid marker on the fibers/article. More than one spray bar may be positioned at more than one location along the conveyor belt. The spray bar may be operatively linked to one or more reservoirs, and the reservoirs may store the solution comprising the nucleic acid marker.

In an exemplary embodiment of the invention, the device for marking fibers or an article may include a regulator (e.g., the metering control shown in FIGS. 2 and 3) associated with the delivery mechanism. The regulator may be adapted to regulate an amount of the solution comprising the nucleic acid marker deposited by the delivery mechanism through the one or more outlets. The regulator may also be at any desired position associated with the delivery mechanism to regulate the amount of solution comprising the nucleic acid marker deposited. For example, the regulator may be positioned along a stream of the solution comprising the nucleic acid marker exiting the delivery mechanism. The regulator may regulate, for example, a flow rate, a flow pressure or a deposition rate of the solution comprising the nucleic acid marker. The regulator may be adjusted manually or automatically. The regulator may be automated, for example, by being monitored and/or adjusted by a computer system.

The regulator may regulate, for example, a flow rate, a flow pressure or a deposition rate of the solution comprising the nucleic acid marker at each individual outlet or may regulate all of the one or more outlets simultaneously. The regulator may regulate the deposition rate of the solution comprising the nucleic acid marker according to the rate of the conveyor belt. For example, if the conveyor belt is moving at a slower relative speed, then the regulator may adjust the deposition rate of the solution comprising the nucleic acid marker to be slower. For example, if the conveyor belt is moving at a relatively high speed, then the regulator may adjust the deposition rate of the solution comprising the nucleic acid marker to keep up with the rate of the conveyor belt. The regulator may be used to adjust the deposition rate of the nucleic acid marker solution appropriate for the number or amount of the fibers or articles on the conveyor belt.

The regulator may regulate a deposition rate of the solution comprising the nucleic acid marker to achieve a desired water content concentration of the fibers/article by regulating an amount of the solution comprising the nucleic acid marker (e.g., an aqueous solution) deposited onto the fibers/article. For example, the water content concentration of processed cotton that has not been marked with the solution comprising the nucleic acid marker may generally be maintained at approximately 8.5% w/w of water per total weight of cotton. The water content of processed wool that has not been marked with the solution comprising the nucleic acid marker may generally be maintained at approximately 12% w/w of water per total weight of wool.

In an exemplary embodiment of the invention, the device for marking fibers or an article may include a measurement apparatus associated with the delivery mechanism. The measurement apparatus may be adapted to measure an amount of the solution comprising the nucleic acid marker deposited by the delivery mechanism. The measurement apparatus may be located at any desired position associated with the delivery mechanism to measure the amount of solution comprising the nucleic acid marker deposited by the delivery mechanism through the one or more outlets. For example, the measurement apparatus may be positioned along a stream of the solution comprising the nucleic acid marker exiting the delivery mechanism. The measurement apparatus may measure, for example, a flow rate, a flow pressure or a deposition rate of the solution comprising the nucleic acid marker. The measurement apparatus may measure, for example, the flow rate of the solution comprising the nucleic acid marker through an individual outlet. The measurement apparatus may be manually or automatically controlled. The measurement apparatus may be controlled by a computer system. The measurement apparatus may provide a signal to the regulator to allow the regulator to adjust the deposition rate of the solution comprising the nucleic acid marker. The measurement apparatus may provide a signal to the regulator to adjust the deposition rate of the solution comprising the nucleic acid marker onto the fibers/article to maintain the desired water content concentration. A computer system may be used to monitor and control the regulator and the measurement apparatus.

Authentication of a Marked Article

The nucleic acid marker may be used to identify specific characteristics of a fibrous material such as cotton or an article that includes the marked fibrous material. For example, the nucleic acid marker may be used to determine whether or not a particular article of interest is authentic by determining whether the article of interest is marked with the nucleic acid marker. By way of example and not of limitation, the nucleic acid marker may be used to encode product information, such as, country of origin for the textile material, origin of the final product, information about the manufacturer, plant identification, product identification and any other desired or related data. The presence of the nucleic acid marker on the fibers or the article may be identified or tracked at any point in the stream of commerce.

The presence of the nucleic acid marker on the fibers or on the an article of interest may be detected by using portable scanners and/or lab verification methods that may include for instance PCR or isothermal amplification followed by any suitable specific marker sequence detection method, such as for instance specific amplicon size detection, or specific marker sequence detection by hybridization with a sequence specific probe. By way of example and not of limitation, test kits, portable scanners and lab verification may be purchased and/or performed by any commercially available source, such as for instance, NEW ENGLAND BIOLABS®, Inc. (Ipswich, Mass.).

According to exemplary embodiments of the invention, the identification data for each nucleic acid marker may be stored in a database. This database may store a plurality of product information, as described above.

In another embodiment, wool may be marked by a method essentially similar to that described above. Wool obtained by shearing a sheep, contains a high level of lanolin (wool wax or wool grease), as well as dead skin, sweat residue, pesticides, and other material such as dirt and vegetable matter. Before the wool can be used for commercial purposes, it is scoured, a process of cleaning the greasy wool. Scouring may be accomplished simply by immersion in a bath of warm water or by an industrial process using detergent and alkali in specialized equipment.

Figure 4:
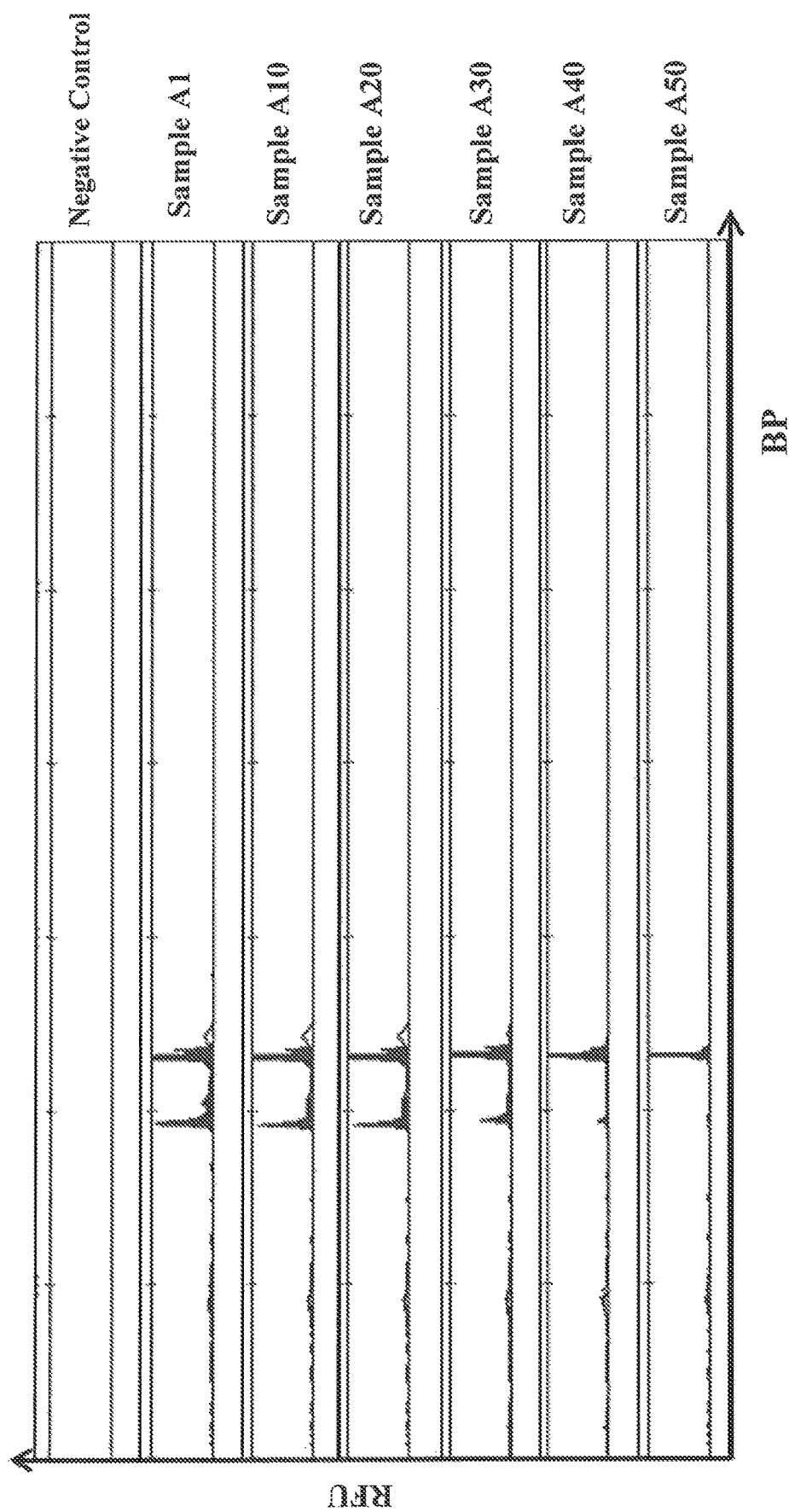
FIG. 4 shows authentication data from capillary electrophoresis traces of PCR products from marked raw wool.

In a test of DNA (SIGNATURE® T DNA marker, Applied DNA Sciences, Inc., Stony Brook, N.Y.) marking of raw wool, alkaline activated double stranded marker DNA was added to a graduated reservoir barrel of 450 L unheated water filled from the local water supply and stirred to mix the aqueous DNA marker solution to achieve a concentration in a range from about 0.1 pg/ml to about 1 ug/ml. The DNA was deposited onto raw wool in a scouring step. A 3,000 kg batch of raw wool (Batch A) was separated from a bale and the separated loose fiber was passed along a conveyor belt under a sprayer depositing the aqueous DNA marker solution from the graduated barrel at a rate of approximately 70 L/hr with the aim of depositing 20 ml per kg raw wool. After an initial 45-60 minutes of spraying, the rate of deposition of the aqueous DNA marker solution was estimated to be higher than the desired 20 ml per kg, so the aqueous DNA marker solution was supplemented with 50 L water and mixed again. Approximately 120 L of this supplemented aqueous DNA marker solution was used to spray the remainder of the 3,000 kg of raw wool. Fifty aliquots of the sprayed raw wool were taken at 2 min. intervals and labeled serially A1 to A50. Samples from each aliquot were sent to Applied DNA Sciences, Inc., where they were subjected to PCR with a primer pair complementary to the two strands of the marker DNA. Amplified products were separated by capillary electrophoresis and demonstrated detectable marker DNA at all time-points tested. (See FIG. 4 showing the results for every tenth sample A1-A50).

Figure 5:
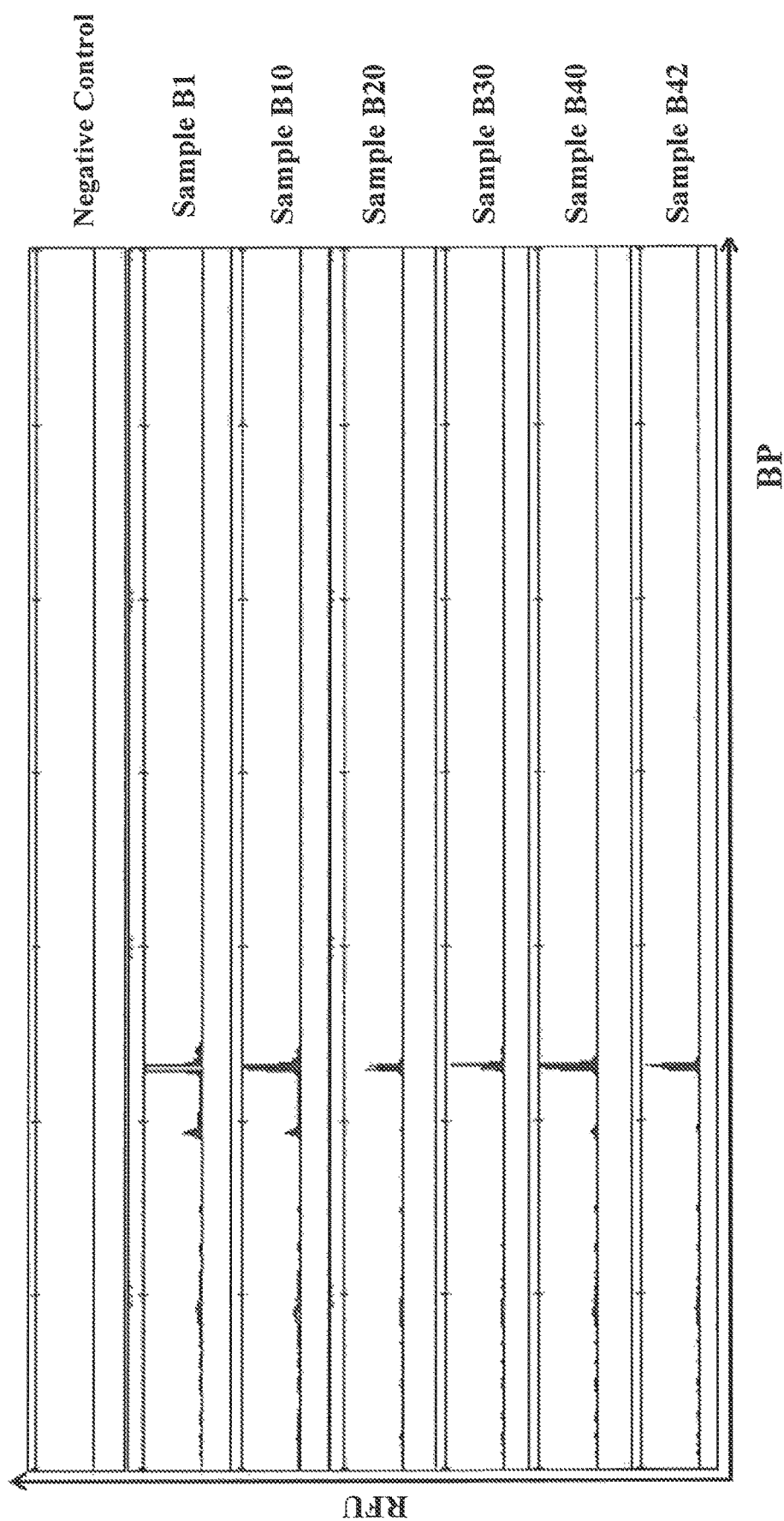
FIG. 5 shows authentication data from capillary electrophoresis traces of PCR products from marked raw wool.

The remaining supplemented aqueous DNA marker solution was bought up to a volume of 450 L again by the addition and mixing of water and 200 L of this second supplemented aqueous DNA marker solution was deposited on a second batch of raw wool of 5,000 kg (Batch B). Fifty aliquots of the sprayed raw wool were taken at 5 min. intervals and labeled serially B1 to B50. Samples from each aliquot were subjected to PCR as before. Amplified products were separated by capillary electrophoresis and demonstrated detectable marker DNA at all time-points tested. (See FIG. 5 showing the results for samples B1-B42).

The remaining second supplemented aqueous DNA marker solution was again bought up to a volume of 450 L again by the addition and mixing of 200 L water; and this third supplemented aqueous DNA marker solution was used to deposit marker DNA on a third batch of raw wool of 25,000 kg at a rate of approximately 50 L/hr to mark the first portion of the third batch of raw wool (Batch C). After 2 hrs of spraying, the volume of the third supplemented aqueous DNA marker solution was again made up to 450 L with water and mixed to form the fourth supplemented aqueous DNA marker solution, which was used to continue spraying Batch C for 2 hours at the same rate of spray deposition onto the raw wool.

Figure 6:
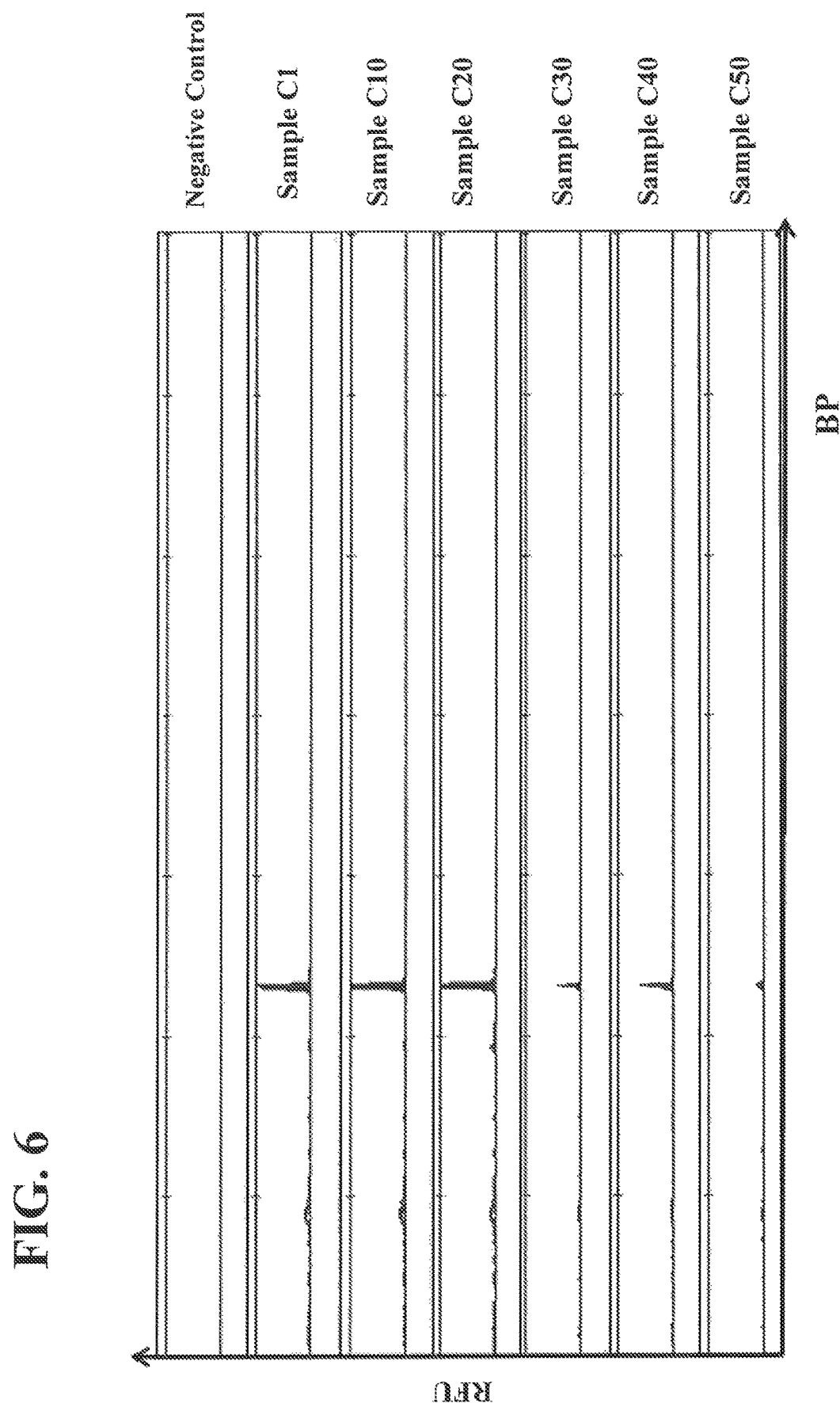
FIG. 6 shows authentication data from capillary electrophoresis traces of PCR products from marked raw wool.

The process of supplementing the previously supplemented aqueous DNA marker solution to make up the volume to 450 L and mixing, followed by spraying for two hours and repeating the supplementing and mixing and spraying process was repeated twice more and the last 450 L was used to mark the remainder of the 25,000 kg of the separated bale of Batch C. Fifty aliquots of the sprayed raw wool were taken at 15 min. intervals and labeled serially C1 to C50. Samples from each aliquot were subjected to PCR as before. Amplified products were separated by capillary electrophoresis and demonstrated detectable marker DNA at all time-points tested. FIG. 6 shows results for samples C1-050 demonstrating that less of the amplified DNA was detected in the fibers marked with the most diluted marker DNA solutions.

Figure 7:
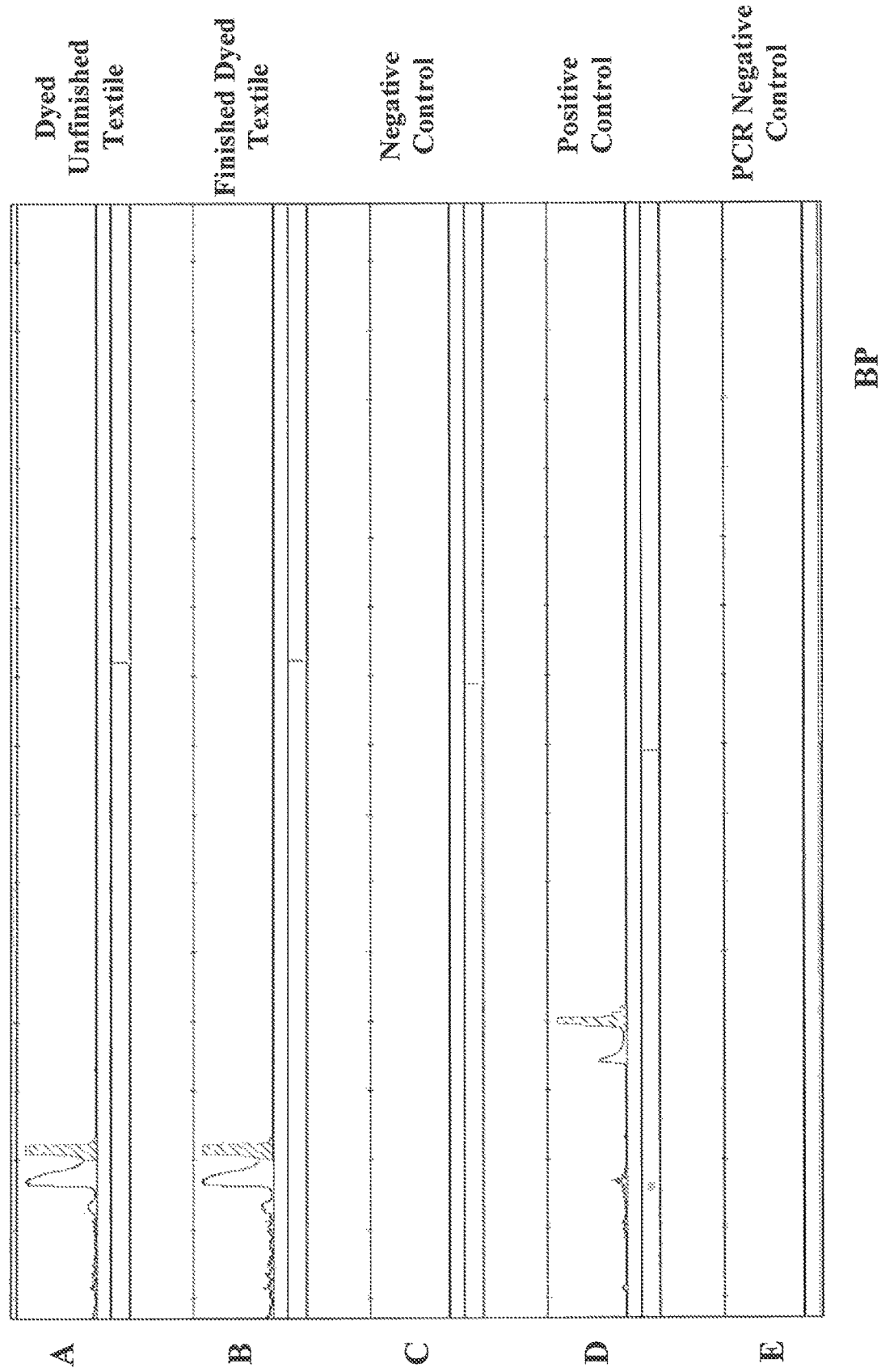
FIG. 7 shows authentication data from capillary electrophoresis traces of PCR products from unfinished and finished textile articles.

FIG. 7 shows authentication data from samples from a finished and an unfinished textile article marked with a SIGNATURE® T DNA marker. The X axis represents a number of base pairs (BP) and the Y axis represents relative fluorescence units (RFU). In FIG. 7, the shaded peak in lane A indicates the presence of a nucleic acid marker (e.g., DNA) was detected in an unfinished textile article. The shaded peak in lane A indicates that multiple copies of a specific amplicon copied by PCR from the nucleic acid marker (e.g., in this case DNA) was detected. The shaded peak in lane B indicates the presence of the same nucleic acid marker as in lane A in a finished textile article. The shaded and unshaded peaks in lanes A and B are substantially similar in size, which indicates qualitatively similar amounts of nucleic acid marker were present in both the finished and unfinished textile articles. Lane C represents a negative control in which the textile had not been marked with the nucleic acid marker. The absence of a peak in lane C indicates that a false positive result has not been detected. Lane D represents a PCR positive control. The peaks in lane D are at a different position than the peaks in lanes A and B because the PCR positive control employed a different DNA sequence having a different number of base pairs than the nucleic acid marker identified in lanes A and B, but demonstrate that the PCR amplification successfully copied amplicons from the control DNA sequence. The presence of the peak in lane D indicates that the PCR reaction proceeded as expected. The lack of a peak in lane E serves as a negative PCR control and further indicates that the PCR reaction was dependent on DNA marker.

Figure 8:
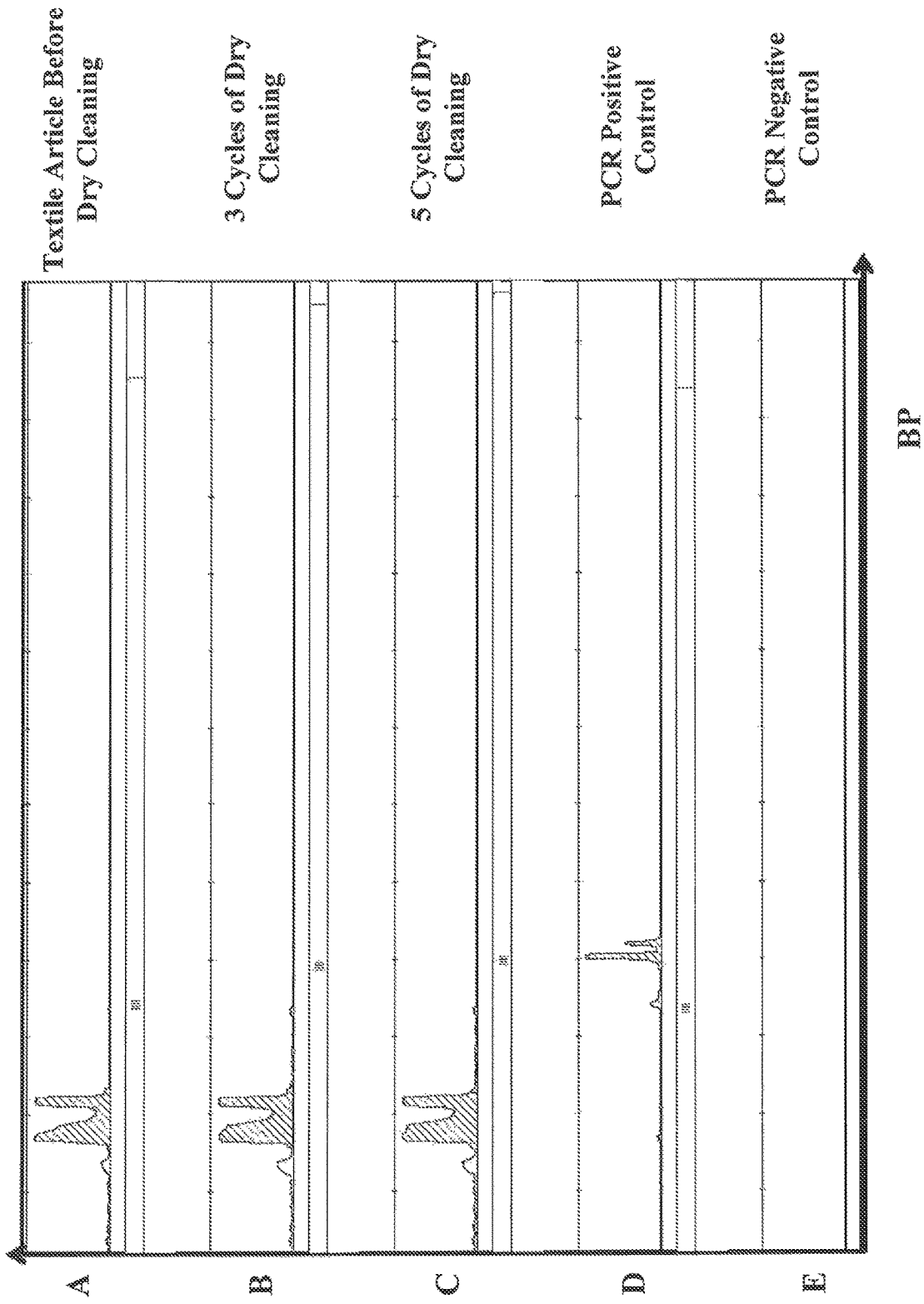
FIG. 8 shows authentication data from capillary electrophoresis traces of PCR products from textile articles before and after multiple cycles of dry cleaning the textile articles.

FIG. 8 shows authentication data from samples from DNA-marked textile articles produced essentially as described above, before and after multiple cycles of dry cleaning the textile articles. The X axis represents a number of base pairs (BP) and the Y axis represents relative fluorescence units (RFU). In FIG. 8, the shaded peak in lane A indicates the presence of a nucleic acid marker (e.g., DNA) was detected in a textile article before dry cleaning. The shaded peak in lane B indicates the presence of the nucleic acid marker was detected after 3 cycles of dry cleaning. The shaded peak in lane C indicates the presence of the nucleic acid marker was detected after 5 cycles of dry cleaning. The shaded peaks in lanes B and C have substantially the same size and position, which indicates that the same nucleic acid marker (i.e., a nucleic acid having the same number of base pairs (BP) is identified) is present in the samples tested in lanes B and C as in lane A, and the nucleic acid marker is present in substantially the same amount as in lane A. Thus, dry cleaning does not reduce the amount of nucleic acid marker present in a marked textile article. Lane D represents a PCR positive control. The peaks in lane D are at a different position than the peaks in lanes A, B and C because the PCR positive control employed a different DNA sequence having a different number of base pairs than the nucleic acid marker identified in lanes A, B and C. The presence of the peak in lane D indicates that the PCR reaction proceeded as expected. The lack of a peak in lane E serves as a negative PCR control and further indicates that the PCR reaction was dependent on DNA marker.

Figure 9:
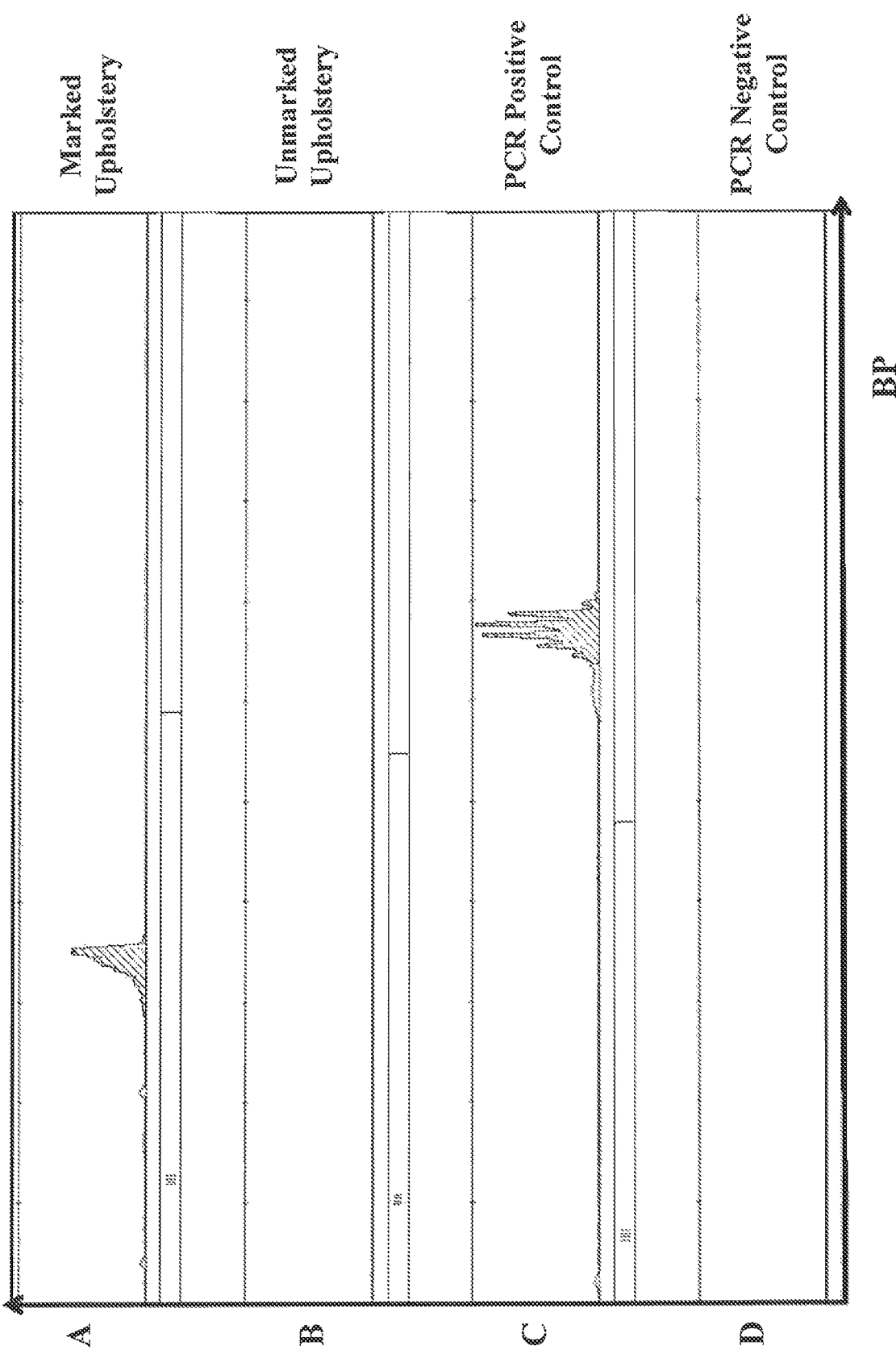
FIG. 9 shows authentication data from capillary electrophoresis traces of PCR products from an upholstery textile made from fibers marked with a nucleic acid marker.

FIG. 9 shows authentication data from capillary electrophoresis traces of PCR products from an upholstery textile marked with a nucleic acid marker prepared essentially as described above. The X axis represents a number of base pairs (BP) and the Y axis represents relative fluorescence units (RFU). In FIG. 9, the shaded peak in lane A indicates the presence of the nucleic acid marker (i.e., DNA) was detected in a sample of marked upholstery after a typical finishing process to prepare upholstery for commercial sale. Lane B represents a test for the presence of the nucleic acid marker in an unmarked upholstery sample to serve as a negative control. The absence of a peak in lane B indicates that a false positive result has not been detected. Lane C represents a PCR positive control. The peaks in lane C are at a different position than the peaks in lane A because the PCR positive control employed a different DNA sequence having a different number of base pairs than the nucleic acid marker identified in lane A. The presence of the peak in lane C indicates that the PCR reaction proceeded as expected. The lack of a peak in lane D serves as a negative PCR control and further indicates that the PCR reaction proceeded as expected.

Figure 10:
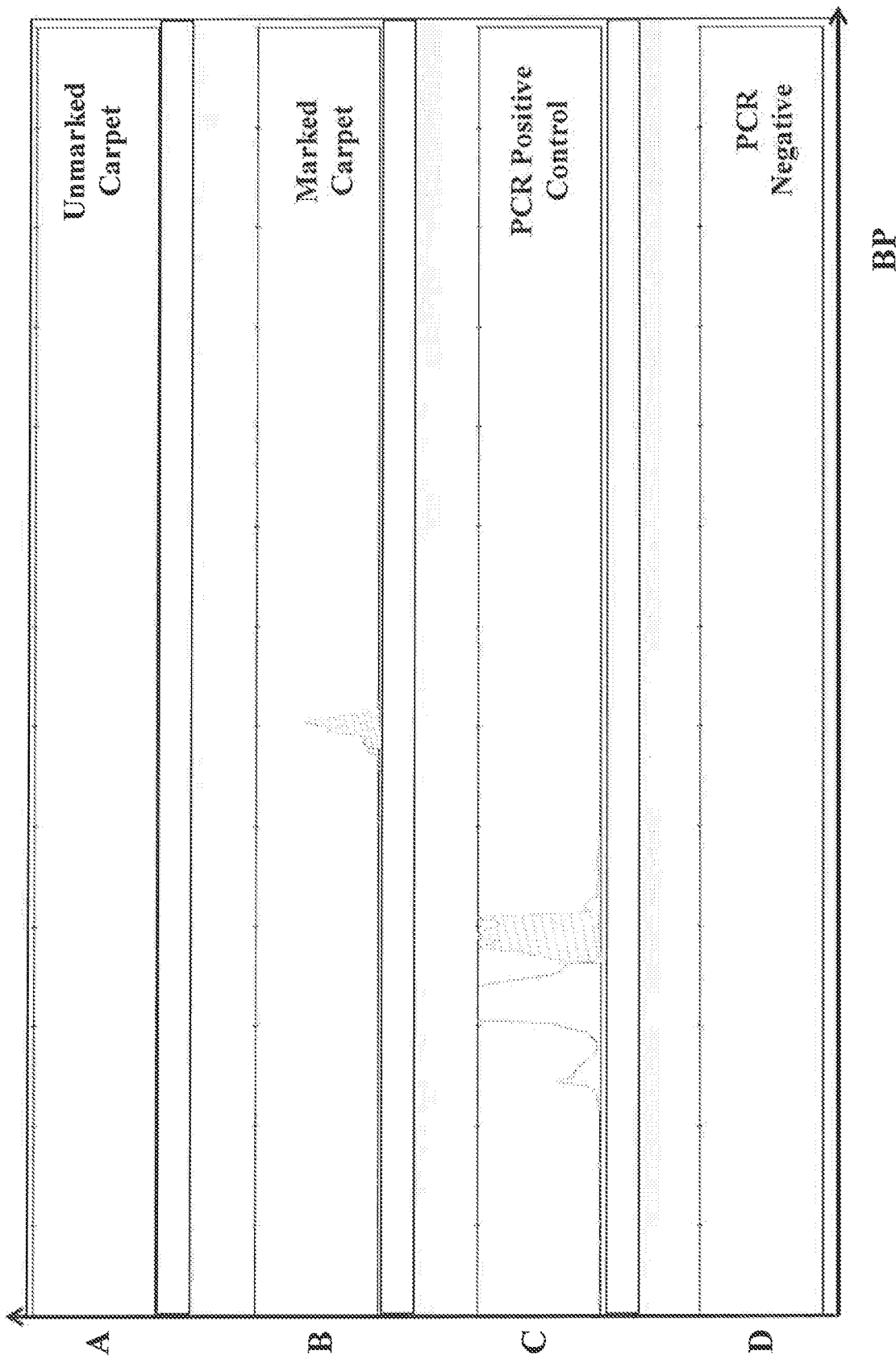
FIG. 10 shows authentication data from capillary electrophoresis traces of PCR products from carpet made from fibers marked with a nucleic acid marker.

FIG. 10 shows authentication data from capillary electrophoresis traces of PCR products from carpet marked with a nucleic acid marker prepared essentially as described above. The X axis represents a number of base pairs (BP) and the Y axis represents relative fluorescence units (RFU). In FIG. 10, the shaded peak in lane B indicates the presence of the nucleic acid marker (i.e., DNA) was detected in a sample of marked carpet after a typical finishing process to prepare a carpet for commercial sale. Lane A represents a test for the presence of the nucleic acid marker in an unmarked carpet sample to serve as a negative control. The absence of a peak in lane A indicates that a false positive result has not been detected. Lane C represents a PCR positive control. The peaks in lane C are at a different position than the peaks in lane A because the PCR positive control employed a different DNA sequence having a different number of base pairs than the nucleic acid marker identified in lane B. The presence of the peak in lane C indicates that the PCR reaction proceeded as expected. The lack of a peak in lane D serves as a negative PCR control and further indicates that the PCR reaction proceeded as expected. Similar results of DNA marking tests were demonstrated with DNA marking of wool during the roving process showing detection of specific PCR amplicon products of lengths characteristic of the marker DNA. (A roving is a long and narrow bundle of fiber. Rovings are produced during the process of making spun yarn from wool fleece, raw cotton, or other fibers).

Likewise, testing of processed wool after DNA marking and dying with a light blue dye yielded readily detectable characteristic PCR amplicons, showing that the alkaline activated DNA marker was distributed throughout the processed wool batches and could be detected after extensive processing of the woolen fibers or yarn. Furthermore the DNA marker was detectable by PCR and capillary electrophoresis in samples of the fibers of the final manufactured carpet products and in the upholstery fabric produced from the DNA marked woolen fibers or yarn.

DNA Marking of Cotton in an Air Flow Duct (Lint Flue) System

Figure 11:
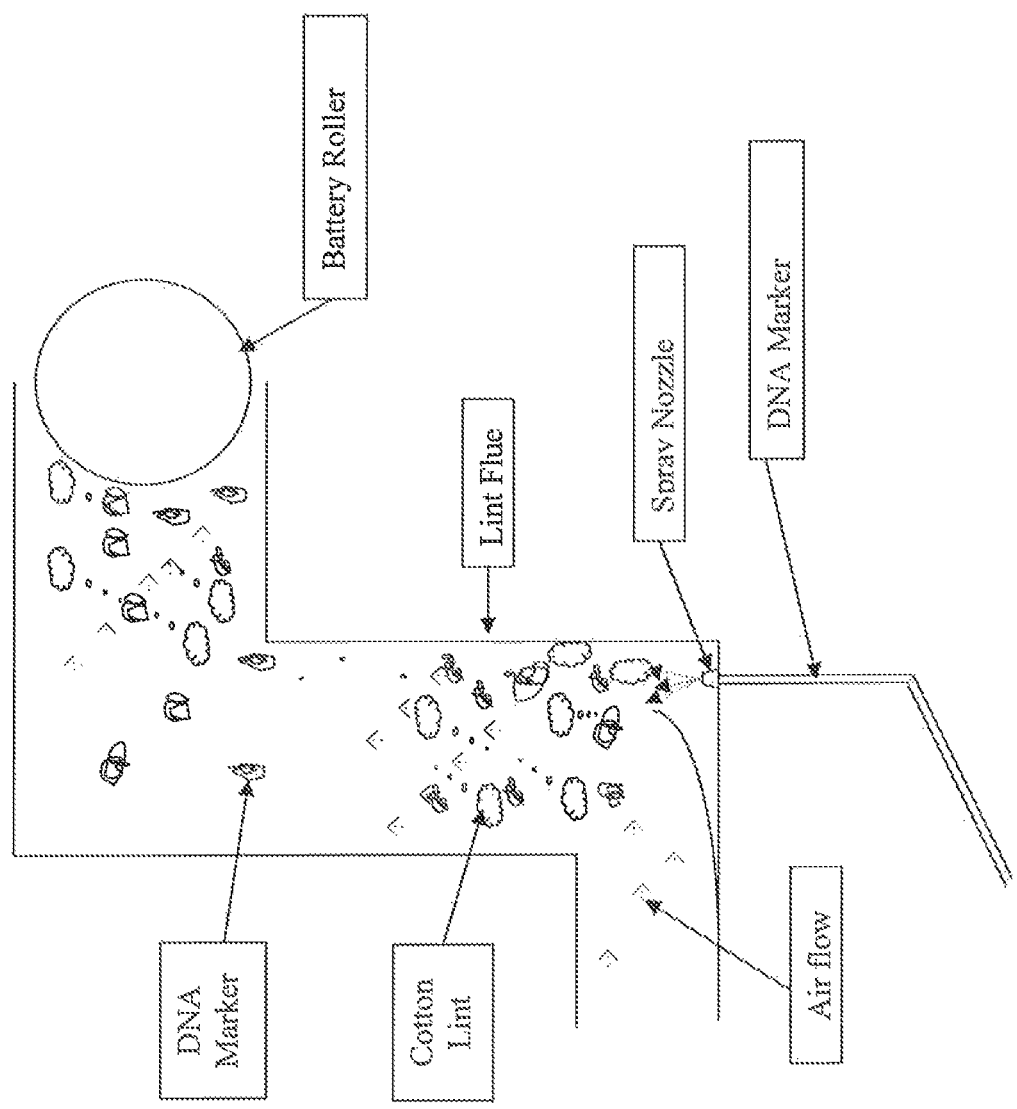
FIG. 11 Shows a schematic of a Lint Flue system useful for marking cotton fibers with DNA according to one embodiment of the invention.

DNA marker can be introduced at any stage of the processing of cotton. For instance and without limitation, the DNA marker may be introduced in any of the following processes: washing, scouring, ginning, carding, combing, roving, spinning, reeling, winding, sizing, bundling, spooling, weaving, knitting or finishing stage of the textile manufacturing process. In the embodiment shown schematically in FIG. 11 cotton fiber lint is forced though a 3 ft diameter Lint Flue by forced air. The DNA marker solution is prepared by dilution into water filtered through a 3 micron filter using a reverse osmosis system. Alkaline activated DNA marker solution including purified natural carrier DNA or artificial carrier DNA of random sequences at a concentration of 46 μg/L prepared as described above is delivered at a rate of 33 ml/min from a 55 gal. (approx. 200 L) reservoir or mixing tank into the filtered water stream flowing at a rate of 1.5 L/min and the DNA solution diluted in this water stream is sprayed through the spray nozzles into the lint flue in DNA:water droplets of less than 200 microns diameter, optimally with a mean diameter of 10-50 microns. The cotton lint ginned from a 25,000 lb block bale is blown through the air flow in the lint flue at a rate of 16,000 cu.ft/min. through the 50 ft length of the 3 ft diameter lint flue, during which the droplets of DNA marker solution are mixed in the turbulent forced air stream to thoroughly mix and evenly coat the marker DNA solution onto the cotton fibers of the cotton lint. The DNA marker solution is adsorbed by the cotton lint along with water added for rehydration, replacing water content lost during heating and drying cycles in the processing of the cotton lint, which is then compressed over a battery condenser/roller to produce a continuous blanket-like lap. The DNA-marked cotton lap is then folded and compressed into 500 lb bales for distribution. DNA marking tests demonstrated that the marker DNA used for marking the cotton lint in the lint flue was detectable as specific PCR amplicon products of lengths characteristic of the marker DNA.

The disclosures of each of the references, patents and published patent applications disclosed herein are each hereby incorporated by reference herein in their entireties. In the event of a conflict between a definition herein and a definition provided in a patent or publication incorporated herein by reference, the definition provided herein is intended. While the invention has been shown and described with reference to exemplary embodiments thereof, it will be understood by those of ordinary skill in the art that various changes in form and detail may be made therein without departing from the spirit and scope of the invention.

What is claimed is:

1. A method of DNA marking raw cotton fiber lint, the method comprising:

providing a plurality of raw cotton fiber lint in a ginning process;

forcing the raw cotton fiber lint through a duct by forced air;

emitting a DNA marker solution consisting of a double stranded DNA marker of a known sequence and reverse osmosis filtered water at a double stranded DNA marker concentration of 1 attogram per milliliter of filtered water to 1 microgram per milliliter of filtered water into the duct via a delivery mechanism comprising one or more outlets in fluid communication with the duct;

wherein the DNA marker solution is evenly deposited on the raw cotton fiber lint; and wherein the DNA marker solution is delivered at a user defined flow rate through the one or more outlets into the duct.

2. A method of authenticating a cotton material comprising:

separating cotton fiber lint from cotton seeds, thereby creating a plurality of raw cotton fiber lint;

forcing the raw cotton fiber lint through a duct by forced air;

evenly depositing a DNA marker solution consisting of a double stranded DNA marker of a known sequence and reverse osmosis filtered water at a double stranded DNA marker concentration of 1 attogram per milliliter of filtered water to 1 microgram per milliliter of filtered water onto the raw cotton fiber lint passing through the duct, the depositing being performed with a delivery mechanism comprising spray nozzles spraying the DNA marker solution into the duct at a user defined flow rate;

thereby producing DNA marked raw cotton fiber lint; and obtaining a sample of DNA marked raw cotton fiber lint and assaying the sample of DNA marked raw cotton fiber lint for the presence of the DNA marker via polymerase chain reaction (PCR) or isothermal amplification to create an amplified product;

and subjecting the amplified product to a specific sequence detection method thereby determining whether the DNA marked raw cotton fiber lint is authentic or counterfeit.

3. The method as defined in claim 1, wherein the DNA marker is comprised of DNA and an optical reporter.

4. The method as defined in claim 1, wherein droplets of DNA marker solution are mixed with the raw cotton fiber lint in a turbulent airstream in the duct.

5. The method as defined in claim 4, wherein the droplets are less than 200 microns in diameter.

6. The method as defined in claim 1, wherein the DNA marker is between 50 base pairs and 500 base pairs in length.

7. The method of claim 1, wherein the DNA is a natural DNA sequence.

8. The method of claim 1, wherein the DNA is an artificial DNA sequence.

9. A method of DNA marking cotton fibers, the method comprising:
   providing a plurality of raw cotton fiber lint in a ginning process;
   forcing the raw cotton fiber lint through a lint flue by a forced air stream;
   filtering water through a reverse osmosis filter;
   mixing a double stranded DNA marker of a known sequence with an alkali activator to create an alkali activated DNA marker and reverse osmosis filtered water at an alkali activated DNA marker concentration of 1 attogram per milliliter of filtered water to 1 microgram per milliliter of filtered water to form an alkaline activated DNA marker solution consisting only of alkali activated DNA, alkali activator and reverse osmosis filtered water; and
   emitting the alkaline activated DNA marker solution into the lint flue forced air stream via a delivery mechanism comprising one or more spray nozzles, whereby the alkaline activated DNA marker solution is mixed in the forced air stream to, thereby, coat the alkaline activated DNA marker solution on the raw cotton fiber lint to mark the raw cotton fiber lint.

* * * * *